(12) United States Patent
Tomioka

(10) Patent No.: US 7,752,917 B2
(45) Date of Patent: Jul. 13, 2010

(54) FATIGUE LIFE ESTIMATING METHOD FOR SPOT WELDED STRUCTURE

(75) Inventor: Noboru Tomioka, Tokyo (JP)

(73) Assignee: Nihon University, Tokyo (JP)

( * ) Notice: Subject to any disclaimer, the term of this patent is extended or adjusted under 35 U.S.C. 154(b) by 606 days.

(21) Appl. No.: 10/556,388

(22) PCT Filed: May 12, 2003

(86) PCT No.: PCT/JP03/05857

§ 371 (c)(1),
(2), (4) Date: Sep. 26, 2008

(87) PCT Pub. No.: WO2004/099761

PCT Pub. Date: Nov. 18, 2004

(65) Prior Publication Data

US 2009/0211366 A1     Aug. 27, 2009

(51) Int. Cl.
*G01N 3/24* (2006.01)
(52) U.S. Cl. .......................... 73/841; 73/850
(58) Field of Classification Search ............ 73/850, 73/841
See application file for complete search history.

(56) References Cited

U.S. PATENT DOCUMENTS

| | | | |
|---|---|---|---|
| 7,448,280 B2 * | 11/2008 | Mons | 73/850 |
| 7,516,673 B2 * | 4/2009 | Dong et al. | 73/760 |
| 7,640,146 B2 * | 12/2009 | Nutwell et al. | 703/2 |
| 2002/0112548 A1 * | 8/2002 | Dong et al. | 73/850 |
| 2007/0090165 A1 * | 4/2007 | Kumagai | 228/101 |

FOREIGN PATENT DOCUMENTS

JP     2003-149130     5/2003

OTHER PUBLICATIONS

Takashi Sawamura et al., "Method of Fatigue Life Estimation for Spot Welded Structures", Society of Automotive Engineers, Inc., 2002-01-2027, 2002.
Harumoto Matsumoto et al.; Transactions of the Society of Automotive Engineers of Japan, vol. 33, No. 3, pp. 103-107, Jul. 15, 2002. Cited in the ISR.

* cited by examiner

*Primary Examiner*—Lisa M Caputo
*Assistant Examiner*—Freddie Kirkland, III
(74) *Attorney, Agent, or Firm*—Westerman, Hattori, Daniels & Adrian, LLP

(57) ABSTRACT

A fatigue life estimating method for a spot welded structure is provided comprising the steps of providing a shell model of a spot welded structure for a finite element method analyzing process, calculating the nominal structural stress on a nugget as the center of the spot welded structure using a disk bending theory and a two-dimensional elastic theory of the elastodynamics with the partial loads exerted on the nugget and the deflection on the circumference of a circle, D in diameter, in which the nugget is located, which have been calculated by the finite element method analyzing process of the shell model, and estimating the fatigue life of the spot welded structure from the nominal structure stress. According to the method, the fatigue life of the spot welded structure can be estimated easily, readily, and accurately.

4 Claims, 27 Drawing Sheets

Circular plate under cross tension $F_z$ and bending moment $M$

Comparison of deflection between present method and exact solution
(D=34.2mm, d=5t$^{1/2}$, t=0.8mm, $F_z$=981N, $M$=0.981N-m)

Distribution of stress $\sigma_r$ along x axis (a)

LP_90_90

(b)

LP_45_90

Pure shear

Stress distribution for pure shear

Bracket sample model

Stress Distribution of spot-welded flat plate with bracket (a) Shell_04 (4 division)    (b) Shell_08 (8 division)
Mesh model for FEM shell analysis Mesh model for FEM solid analysis Comparison of stress $\sigma_r$ between Shell_04 and Shell_08
(LP_90_90)

(a) L plate (b) Flat plate

Comparison of nominal structural stress between FEM solid analysis and present method (Load size 2943N)

DC test piece (a) Tensile shear (b) Cross tension

TS, CT test piece

Fatigue life estimation of spot-welded structures

Loads acting on nugget

Stress distribution for pure shear

Circular plate with inner hole under inner and outer pressures

Radial stress distributions of circular plate

FATIGUE LIFE ESTIMATING METHOD FOR SPOT WELDED STRUCTURE

FIELD OF THE INVENTION

The present invention relates to a fatigue life estimating method for a spot welded structure and particularly to a fatigue life estimating method for estimating the fatigue life of a spot welded structure from a nominal structural stress which has been calculated from the partial load at a nugget in the spot welded structure while producing a finite element method analyzing shell model of the spot welded structure.

BACKGROUND OF THE INVENTION

In the field of automobile research and development, a variety of estimation methods using a computer-aided CAE technology have been proposed progressively for minimizing the weight of vehicles, the length of time for the development, and the number of prototype vehicles. Among of them is estimation of the physical strength of a vehicle which has also been vigorously studied.

The body of a vehicle is generally fabricated by sheet metals. The sheet metals are commonly joined together by spot welding. During the spot welding, the vehicle receives loads which are then transmitted through the welding contacts to every part of the components. In particular, the loads may be intensified at the welding contacts thus declining the physical strength of the vehicle. As the number of the welding contacts is large and the loads are composite or varied in the characteristics, the demand for developing a method of estimating the fatigue life of the spot welding contacts accurately and readily will now be increased.

In response to the demand, a technique for estimating the fatigue life of spot welding contacts is proposed by Dieter Radaj, et al., as disclosed in "Design and Analysis of Fatigue Resistant Welded Structures", Abington Publication, P. 378, 1990, where a disk, D in diameter, having a nugget at the center and separated from the spot welded structure of a vehicle is subjected to FEM shell analysis for calculating the nominal structural stress $\sigma_{ns}$ from partial loads on the nugget and settings of the diameter D saved in a database, whereby the fatigue life of the spot welded structure can be estimated from the nominal structural stress. The fatigue/reliability group of the automobile technology committee has also proposed a similar method concerning the effect of torsion on the structure. The nominal structural stress $\sigma_{ns}$ is a maximum main stress produced at the spot welding contact (nugget).

Each of the methods includes, as shown in FIG. 22, a step S1 of fabricating a spot welded structure, a step S2 of preparing a finite element method analyzing shell model (FEM model) and providing the FEM model with a load data D1, a step S3 of determining six partial forces of the load exerted at the spot welded contact (nugget), a step S4 of calculating the nominal structural stress $\sigma_{ns}$ with settings of D saved in a database D2, and a step S5 of estimating the fatigue life through examining the nominal structural stress $\sigma_{ns}$ with a map of database D3 representing the relationship between the nominal structural stress $\sigma_{ns}$ and the number of cycles to fracture Nf.

However, both the conventional methods allow the nominal structural stress $\sigma_{ns}$ to be calculated using a disk bending theory of the elastodynamics on a disk, D in diameter, as a rigid body having a nugget designated at the center thereof while peel load and bending moment of the partial forces are concerned. The circumferential condition for the disk is based on the fact that no deflection nor tilting in any radial direction is involved as is termed an entire-freedom arresting condition. It is hence not easy for calculating the nominal structural stress $\sigma_{ns}$ on the disk of spot welded structure to determine an optimum of the diameter D of the disk. In the prior art, the diameter D is determined from a database D2 as shown in a flowchart of FIG. 22. It is true that the preparation of the database D2 is also a labor intensive task.

FIG. 23 illustrates a disk 2, D in diameter, separated from a spot welded structure and having a nugget 1 (spot welded contact) designated at the center thereof. The nugget 1 generally receives six partial loads;
1. peel load Fz,
2. bending moments Mx, My,
3. shearing loads Fx, Fy, and
4. torsional moment Mz.

The method by Dieter Radaj et al calculates the nominal structural stress $\sigma_{ns}$, which is a fatigue strength parameter responsive to particularly the torsional moment and the peel load of the six partial loads exerted on the nugget, using the following elements, (1) Peel load $$\sigma_{ns} = 0.69\left(\frac{F_z}{t^2}\right)\ln\left(\frac{D}{d}\right)$$

(2) Bending moment $$\sigma_{ns} = 25.4\left(\frac{M}{dt^2}\right)\left(\frac{d}{D}\right)\Big/ e^{4.8\frac{d}{D}}$$

where D, d, and t are the outer diameter, of the disk 2 having the nugget 1 provided in the center, the diameter of the nugget 1, and the thickness of the disk 2 as shown in FIG. 23 and Fz and M are the peel load and the bending moment exerted on the nugget 1.

Equations 1 and 2 are based on the fact that the disk 2 shown in FIG. 23 has the nugget 1 as a rigid body and is perfectly arrested at the circumference for no strain.

Accordingly, only when the perfect arresting condition for no strain is satisfied, the diameter D may be determined with a favorable setting for calculating the nominal structural stress $\sigma_{ns}$ on a spot welded structure from Equations 1 and 2 and estimating the fatigue life. There may however be seldom the case where the area about the nugget 1, D in diameter, in an actual spot welded structure remains perfectly arrested for no strain. Therefore, it will be a drawback for calculation of the equations to determine the diameter D of the disk 2 to an optimum.

It is assumed for examining the stress responsive to the shearing load Fx and Fy that the shearing load Fx is exerted in the x direction on the center as circular rigid body of an infinite plate which has a diameter of d and acts as a nugget. The stress component $\sigma_x$ along the x direction off the rigid body is then expressed by:

$$\sigma_x = \frac{-F_x}{2\pi t(\kappa+1)} \frac{1}{x}\left\{\left(\kappa - \frac{1}{2}\frac{d^2}{x^2}\right) + 3\right\} \quad (3)$$

$$\kappa = (3-\nu)/(1+\nu) \quad (\text{平面応力})$$

where $\nu$ is the Poisson's ratio. As the nominal structural stress is a maximum main stress at the edge of the nugget, $$\sigma_x = \frac{F_x}{\pi dt} \quad (4)$$

FIG. 24 illustrates a profile of the stress distribution vertical to the loading direction on the outer surface of the center plate of three plates which have been spot welded together and loaded with a tensile shearing force, where $\sigma_o$ is the uniform tensile stress. As apparent, the theoretical result of Equation 3 as the nominal structural stress is closely approximate to the result of FEM three-dimensional elastodynamics analysis at the point close to the nugget. However, the difference between the two results is gradually increased as the point departs from the edge of the nugget. The reason is because Equation 3 approximates zero at the furthest point from the nugget and fails to exhibit the result of the stress $\sigma_o$ at the point close to the nugget.

For example, when a doughnut shaped disk is urged by external pressures from both, outer and inner, sides, its resultant stress is expressed by a particular profile of the distribution. The stress is calculated from:

$$\sigma_r = \frac{a^2}{b^2 - a^2}\left[\left(1 - \frac{b^2}{r^2}\right)p_{in} - \left(\frac{b^2}{a^2} - \frac{b^2}{r^2}\right)p_{ot}\right] \quad (5)$$

$$\sigma_r = -\frac{a^2}{r^2}p_{in} \quad (6)$$

FIG. 26 illustrates comparison between the above profile and its comparative profile from Equation 6 where the doughnut shaped disk is replaced by an infinite plate having an opening provided therein. When the outer pressure is smaller than the inner pressure, the former profile may be similar to the latter profile of the infinite plate. However, when the two, outer and inner, pressures are substantially equal, the stress profiles will significantly be different from each other. This phenomenon may appear in the profile of the stress distribution shown in FIG. 24 where the three plates are spot welded together. It will hence be difficult to calculate the stress at higher accuracy through comparison with that of the infinite plate.

FIG. 27 illustrates a profile of the stress distribution vertical to the loading direction where two, large and small, flat plates are joined to each other by spot welding to simulate a bracketed spot welded joint and loaded at both sides with uniform tensile stresses $\sigma_o$. Since the welded plates remain balanced, the partial loads on the nugget will be zero at the finite element method analysis using a shell element model. It is thus understood that Equation 3 is unfavorable for determining the stress for the case.

It is hence an object of the present invention to provide a fatigue life estimating method for a spot welded structure in which the nominal structural stress is calculated from the deflection, the tilting in one radial direction, the bending moment, the peel load, the shearing force, and the torsional moment on a disk to be examined for optimizing the setting of D and the fatigue life of the disk or spot welded structure is estimated using the nominal structural stress.

It is another object of the present invention to provide a novel method of solving the drawback that as the point to be measured departs from the edge of the nugget, its uniform load tensile stress is increased in the erratic measurement.

DISCLOSURE OF THE INVENTION

For achieving the above object of the present invention, a fatigue life estimating method for a spot welded structure is characterized comprising the steps of: preparing a spot welded structure consisting of two or more plates joined together; providing a shell model from the spot welded structure for a finite element method analyzing process; subjecting the shell model to the finite element method analyzing process to calculate the peel load, the bending moment, the shear force, and the torsional moment as partial forces exerted on a nugget at the center of the spot welded structure as well as the deflection on the circumference of a circle which is D in the diameter and defined to have the nugget at the center; calculating the nominal structural stress responsive to the peel load, the bending moment, the shear force, and the torsional moment using a disk bending theory and a two-dimensional elastic theory of the elastodynamics with the calculations of the partial loads and the deflection, where components $\sigma_r$, $\sigma_\theta$, and $\tau_{r\theta}$ of the nominal structural stress responsive to the shear force and the torsional moment are calculated using a two-dimensional elastodynamics formula $$\sigma_r = a_0 r^{-2} + 2b_0 + \left(\frac{a_1}{r} + 2b_1 r - 2a'_1 r^{-3} + b'_1 r^{-1}\right)\cos\theta +$$
$$\left(\frac{c_1}{r} + 2d_1 r - 2c'_1 r^{-3} + d'_1 r^{-1}\right)\sin\theta +$$
$$\sum_{n=2}^{\infty} \{a_n n(1-n)r^{n-2} + b_n(n+2-n^2)r^n -$$
$$a'_n n(1+n)r^{-n-2} + b'_n(-n+2-n^2)r^{-n}\}\cos n\theta +$$
$$\sum_{n=2}^{\infty} \{c_n n(1-n)r^{n-2} + d_n(n+2-n^2)r^n - c'_n n(1+n)r^{-n-2} +$$
$$d'_n(-n+2-n^2)r^{-n}\}\sin n\theta$$

$$\sigma_\theta = -a_0 r^{-2} + 2b_0 + (6b_1 r + 2a'_1 r^{-3} + b'_1 r^{-1})\cos\theta +$$
$$(6d_1 r + 2c'_1 r^{-3} + d'_1 r^{-1})\sin\theta +$$
$$\sum_{n=2}^{\infty} \{a_n n(n-1)r^{n-2} + b_n(n+2)(n+1)r^n +$$
$$a'_n n(n+1)r^{-n-2} + b'_n(-n+2)(-n+1)r^{-n}\}\cos n\theta +$$
$$\sum_{n=2}^{\infty} \{c_n n(n-1)r^{n-2} + d_n(n+2)(n+1)r^n + c'_n n(n+1)r^{-n-2} +$$
$$d'_n(-n+2)(-n+1)r^{-n}\}\sin n\theta$$

$$\tau_{r\theta} = (2b_1 r - 2a'_1 r^{-3} + b'_1 r^{-1})\sin\theta - (2d_1 r - 2c'_1 r^{-3} + d'_1 r^{-1})\cos\theta +$$
$$\sum_{n=2}^{\infty} \{a_n n(n-1)r^{n-2} + b_n n(n+1)r^n - a'_n n(n+1)r^{-n-2} - b'_n n(n-1)r^{-n}\}$$
$$\sin n\theta -$$
$$\sum_{n=2}^{\infty} \{c_n n(n-1)r^{n-2} + d_n n(n+1)r^n - c'_n n(n+1)r^{-n-2} - d'_n n(n-1)r^{-n}\}$$
$$\cos n\theta$$

(where $a_0$ to $d'_n$ are unknown coefficients determined by the loading condition and the boundary condition), and components $\sigma_r$, $\sigma_\theta$, and $\tau_{r\theta}$ of the nominal structural stress responsive to the bending moment and the peel load are calculated from $$\sigma_r = -D_p \frac{6}{t^2} \left[ M_{r0} + \sum_{n=1}^{\infty} M_{rfn} \cos n\theta + \sum_{n=1}^{\infty} M_{rgn} \sin n\theta \right]$$

$$\sigma_\theta = -D_p \frac{6}{t^2} \left[ M_{\theta 0} + \sum_{n=1}^{\infty} M_{\theta fn} \cos n\theta + \sum_{n=1}^{\infty} M_{\theta gn} \sin n\theta \right]$$

$$\tau_{r\theta} = (1-v)D_p \frac{6}{t^2} \left[ \sum_{n=1}^{\infty} M_{r\theta fn} \sin n\theta + \sum_{n=1}^{\infty} M_{r\theta gn} \cos n\theta \right]$$

where $$M_{r0} = \frac{d^2 f_0}{dr^2} + \frac{v}{r} \frac{df_0}{dr}$$

$$M_{rn} = \frac{d^2 f_n}{dr^2} + \frac{v}{r}\left(\frac{df_n}{dr} - \frac{f_n}{r}n^2\right) \ (i \geq 1)$$

$$M_{rgn} = \frac{d^2 g_n}{dr^2} + \frac{v}{r}\left(\frac{dg_n}{dr} - \frac{g_n}{r}n^2\right) \ (i \geq 1)$$

$$M_{\theta 0} = v\frac{d^2 f_0}{dr^2} + \frac{1}{r}\frac{df_0}{dr}$$

$$M_{\theta n} = v\frac{d^2 f_n}{dr^2} + \frac{1}{r}\left(\frac{df_n}{dr} - \frac{f_n}{r}n^2\right) \ (i \geq 1)$$

$$M_{\theta gn} = v\frac{d^2 g_n}{dr^2} + \frac{1}{r}\left(\frac{dg_n}{dr} - \frac{g_n}{r}n^2\right) \ (i \geq 1)$$

$$M_{r\theta fn} = -\frac{n}{r}\left(\frac{df_n}{dr} - \frac{f_n}{r}\right) \ (i \geq 1)$$

$$M_{rgn} = \frac{n}{r}\left(\frac{dg_n}{dr} - \frac{g_n}{r}\right) \ (i \geq 1)$$

$$f_0 = A_0 + B_0 r^2 + C_0 \ln r + D_0 r^2 \ln r$$

$$f_1 = A_1 r + B_1 r^3 + C_1 r^{-1} + D_1 r \ln r$$

$$f_n = A_n r^n + B_n r^{-n} + C_n r^{n+2} + D_n r^{-n+2}$$

$$g_1 = A_1' r + B_1' r^3 + C_1' r^{-1} + D_1' r \ln r$$

$$g_n = A_n' r^n + B_n' r^{-n} + C_n' r^{n+2} + D_n' r^{-n+2}$$

(where r and θ are the polar coordinates, E is the Young's modulus, ν is the Poisson's ratio, t is the thickness, and $A_0$ to $D'_n$ are unknown coefficients determined by the loading condition and the boundary condition); and estimating the fatigue life of the spot welded structure from the nominal structural stress.

According to a feature of the invention, a disk having a diameter of D and including the nugget of interest at the center is separated from the spot welded structure and stained at the outer edge when loaded at the nugget with partial forces of peel load, bending moment, shear load, and torsional moment for calculating the nominal structural stress. This allows no database of the D diameter to be needed and the troublesome task for determining an optimum of the D diameter to be eliminated. As the result, the fatigue life of the spot welded structure can be estimated easily and readily.

The fatigue life estimating method for a spot welded structure may be modified in which the two or more plates are at least a flat plate and an L channel while the shell model for the finite element method analyzing process is marked with a square having one side arranged equal to the flange width of the L channel and including the nugget at the center, the square divided radially by two at the nugget, radially by four at the other area than the nugget, and circumferentially by eight.

The fatigue life estimating method for a spot welded structure may be modified in which the step of estimating the fatigue life of the spot welded structure includes subjecting the spot welded structure to a tensile shear fatigue test, a peal fatigue test, and a component load fatigue test to produce a map representing the relationship between the nominal structural stress and the number of cycles to fracture and determining the number of cycles to fracture at the nominal structural stress through examining the map.

Furthermore, the fatigue life estimating method for a spot welded structure may be modified in which said nominal structural stress is a function responsive to not only the shear force (F), and the torsional moment (Mz), but also responsive to the deflections u and v along the directions of γ and θ respectively of polar coordinates on the circumference of assumed spot diameter, and the deflections u and v are calculated from the distortions $\epsilon_r$ and $\epsilon_\theta$ along the directions of γ and θ respectively.

BEST MODES FOR EMBODYING THE INVENTION

Some embodiments of the present invention will be described in the form of a fatigue life estimating method for a spot welded structure.

Figure 1:
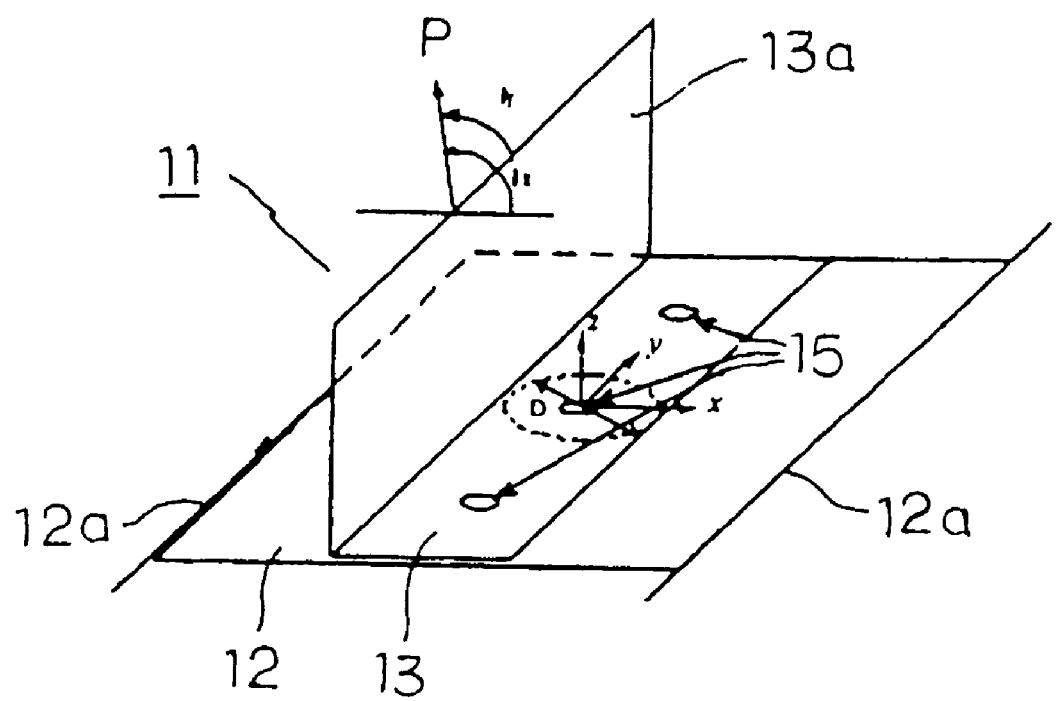
FIG. 1 is a perspective view of an LP model used in a fatigue life estimating method for a spot welded structure according to the present invention.

The description is based on an LP model 11 as a simple spot welded structure shown in FIG. 1. The LP model 11 is a combination of a plat plate 12 and an L channel 13 welded to each other at three spot welded contacts. It is assumed that when the flat plate 12 is perfectly arrested at its two opposite sides 12a and 12b for no strain, the L channel 13 is loaded at the upper end of its vertical portion 13a in various directions by a pressure P and the nominal structural stress $\sigma_{ns}$ is calculated at the nuggets 15 along the center line.

Figure 2:
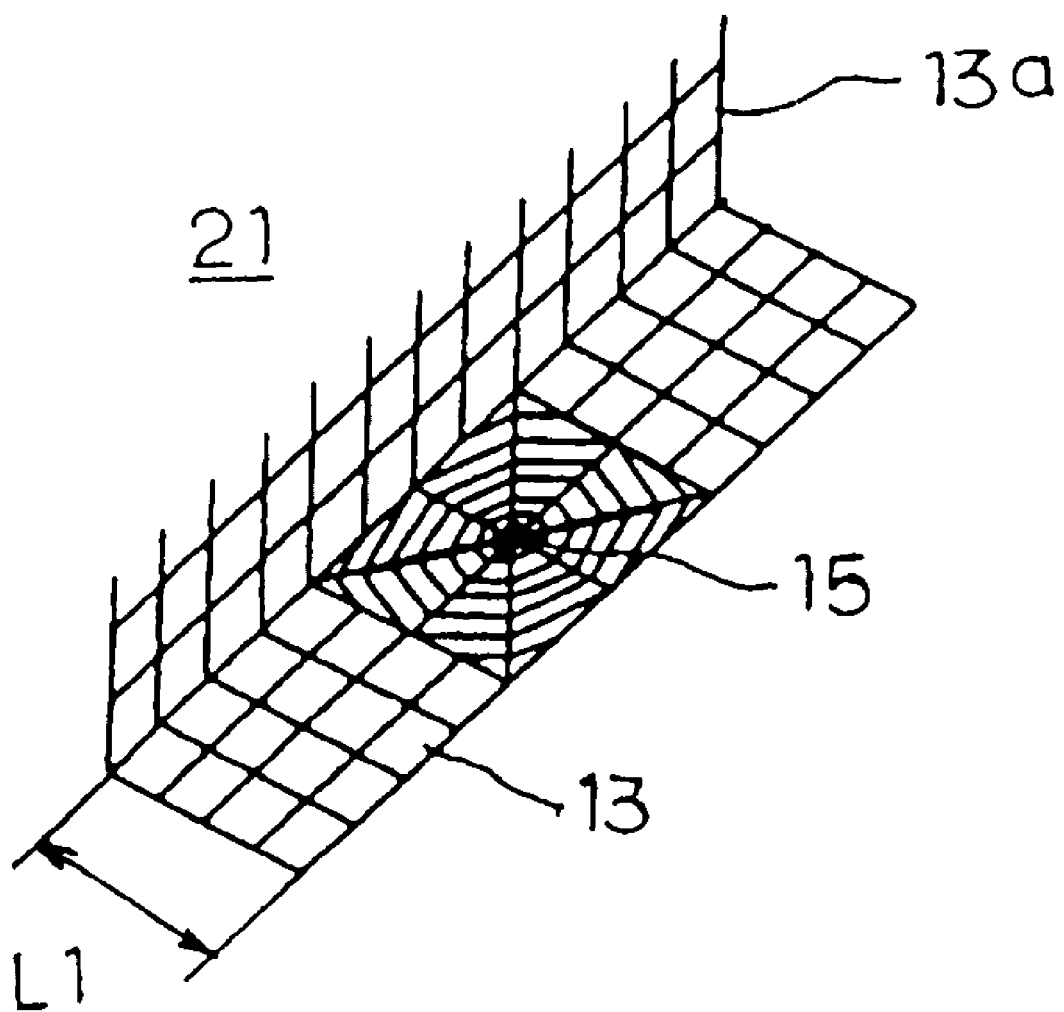
FIG. 2 is an enlarged perspective view showing about a nugget defined on a shell model for finite element method analyzing process in the fatigue life estimating method for a spot welded structure of the present invention.

The action starts with preparing a finite element method analyzing shell model 21. The analyzing model 21 is prepared from a shell element employed commonly in the body strength analyzing process for finite element method analyzing of the LP model 11. FIG. 2 is an enlarged view of the LP shell analyzing model where the nugget 15 is enlarged. The nugget 15 and its adjacent area is expressed by a square having one side arranged equal to the flange width L1 and separated into small segments while the other area of the model is denoted by a rough grating pattern of small squares. As shown in FIG. 2, the nugget 15 is divided radially by two while the other area than the nugget in the square is divided radially by four. The square is also divided circumferentially by eight.

The finite element method analyzing shell model 21 is then subjected to the finite element normal elastic analyzing process for determining partial forces exerted on the nugget 15. The deflection and tilting in a radial direction at the (eight) vertices of one particular octagonal shape is calculated from the deflection (deflection in the z direction) at the nodes located along the diagonal lines (four shown in FIG. 2) extending across from the center of the nugget 15. The octagonal shape for determining the deflection and tilting in a radial direction is inscribed in the circle of D in diameter denoted by the dotted line shown in FIG. 1. The deflection and tilting is then used as a supporting condition at the circumference of the circle.

Figure 3:
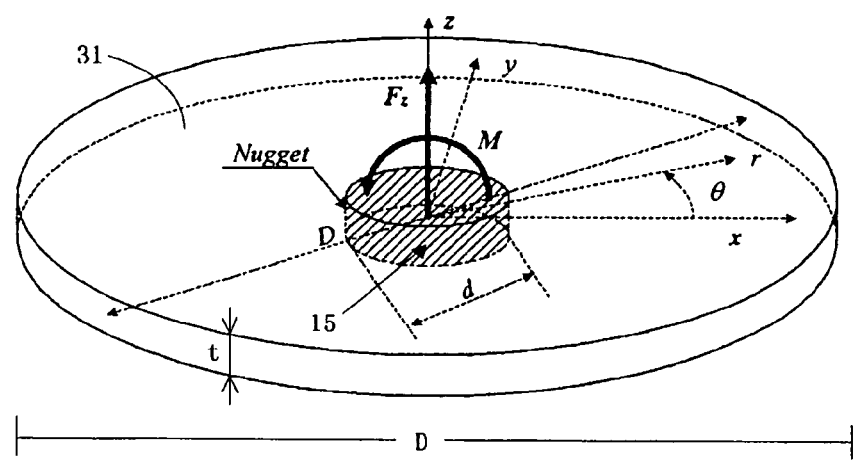
FIG. 3 is an explanatory view of a disk, D in diameter, in the fatigue life estimating method for a spot welded structure of the present invention.

As the circle denoted by the dotted line in FIG. 1, a disk 31 of D in diameter having the nugget 15 at the center is separated from the LP model 11 of the spot welded structure. The disk 31 of D in diameter is illustrated in FIG. 3. The disk 31 circumscribes the octagonal shape. The stress and strain of the disk 31 is then calculated using a disk bending theory of the elastodynamics. The external pressure exerted on the disk 31 is partial stresses on the nugget 15. More specifically, the pressure is expressed by a load Fz in the z direction and a bending moment M (combination of Mx and My).

The supporting condition at the circumference of the disk 31 is the deflection and tilting of the octagonal shape. Since the support condition is a discrete value, its circumferential distribution is approximated to a Fourier series which is then used as the boundary or circumference supporting condition.

The nominal structure stress formulas of Equations 1 and 2 proposed by Dieter Radaj et al are based on the fact that the circumference supporting condition for the disk 31 shown in FIG. 3 resides in no deflection of the shape. It is hence unfavorable in the accuracy to determine the nominal structural stress $\sigma_{ns}$ at the nugget 15 shown in FIG. 1 using the nominal structure stress formulas of Equations 1 and 2 proposed by Dieter Radaj et al because the circumference of the disk 31 of D in diameter provided as a spot welded structure shown in FIG. 1 is not perfectly arrested for no strain and its supporting condition is different from that (no deflection allowed) of Dieter Radaj et al when the parameter D in Equations 1 and 2 represents the diameter of the circle denoted by the dotted line shown in FIG. 1. For compensation, the parameter D in Equations 1 and 2 is modified. However, the modification depends largely on the type and the loading condition of the stop welded structure. It is thus necessary to determine the nominal structural stress $\sigma_{ns}$ using the database D2 which has been prepared from various modifications of D.

In the fatigue life estimating method for a spot welded structure according to the present invention, the circumference supporting condition for the disk shown in FIG. 3 considers an actual deflection at the circle of D in diameter on the spot welded structure, thus ensuring an estimation at higher accuracy of the nominal structural stress $\sigma_{ns}$. Also, the method of the embodiment eliminates a troublesome step of correcting the parameter D to a desired setting and needs no preparation of the database D2 for D.

The nominal structural stress $\sigma_{ns}$ responsive to the shear component (Fx, Fy) and the torsion in the nugget receiving load or the composite load which is a sum of the six partial loads is calculated using a theoretical formula which will be described later in more detail. Then, the fatigue life at the nominal structural stress $\sigma_{ns}$ calculated by the foregoing method is estimated from a combination of the nominal structural stress $\sigma_{ns}$ and the number of cycles to fracture Nf in a database produced by a simple test piece of the spot welded structure subjected to a fatigue test under a composite load.

Figure 4:
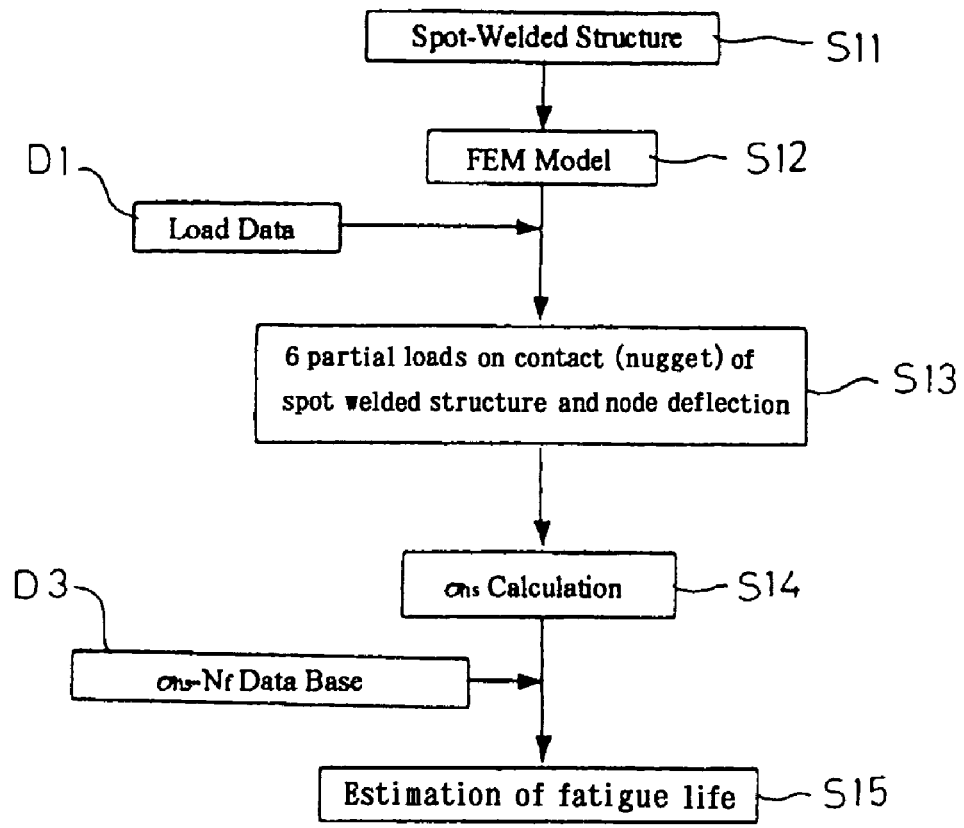
FIG. 4 is a flowchart showing the fatigue life estimating method for a spot welded structure according to the present invention.

FIG. 4 illustrates a flowchart of the estimation procedure.

As shown in FIG. 4, the procedure starts with a step S11 of fabricating a spot welded structure, a step S12 of preparing a finite element method analyzing shell mode (FEM model), and a step S13 of subjecting the FEM model to a finite element normal elastic analyzing process with the use of a load data D1 to determine the six partial loads and the deflection at each node on the spot welded contact (nugget). This is followed by a step S14 of calculating the nominal structural stress $\sigma_{ns}$ from the six partial loads and the deflections at the nodes and a step S15 of referring the database D3 to compare the nominal structural stress $\sigma_{ns}$ with its reference levels predetermined through a series of experiments for determining the number of cycles to fracture Nf and thus the fatigue life.

Figure 21:
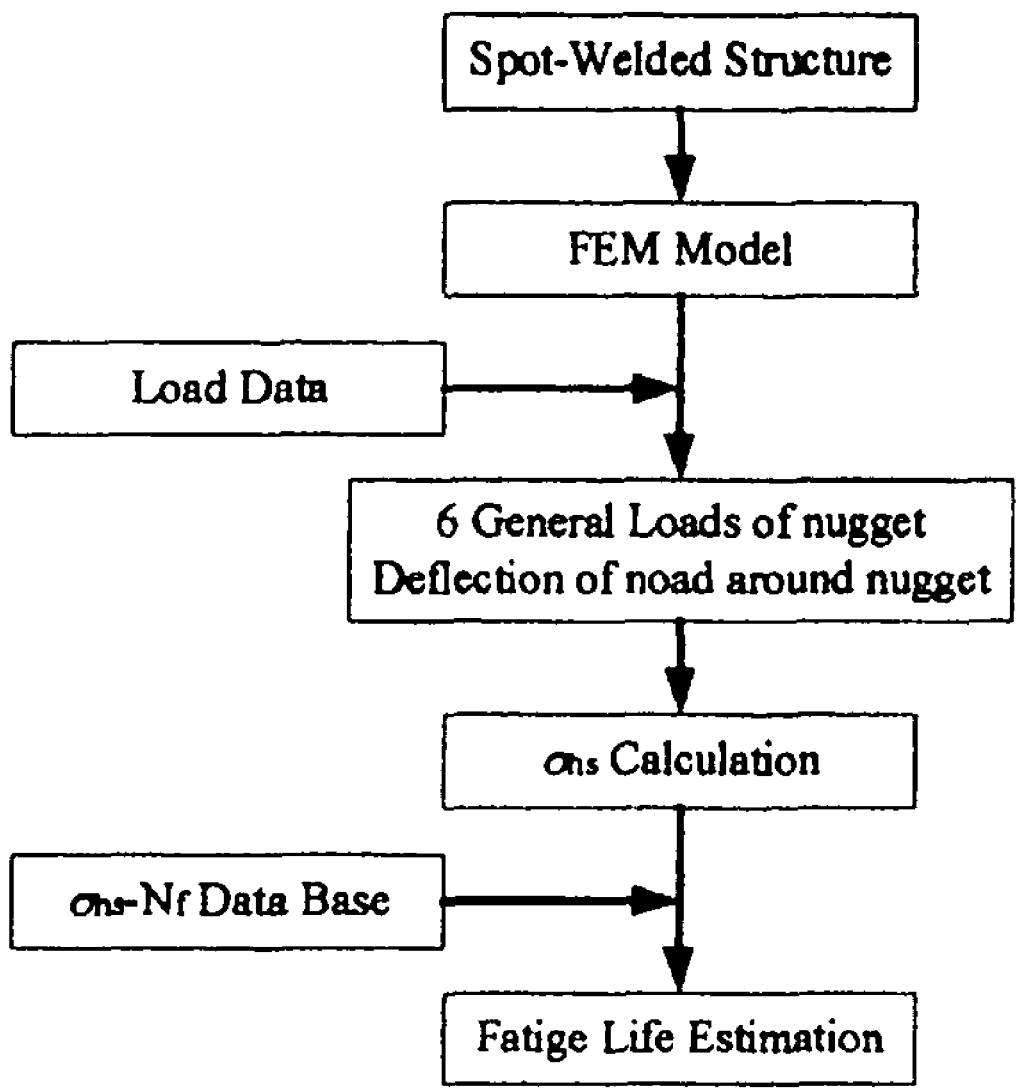
FIG. 21 is a flowchart showing the fatigue life estimating method for a spot welded structure of the present invention.

As comparing with the procedure shown in FIG. 21, this requires non of the database D2 for calculating the nominal structural stress $\sigma_{ns}$.

The method according to the present invention is unique for calculating the nominal structural stress $\sigma_{ns}$ responsive to the bending load while eliminating the troublesome step of determining the optimum of D.

It is now assumed that the disk has an outer diameter D and a thickness t and its nugget (d in diameter) is loaded with a peel force Fo and a bending moment M as shown in FIG. 3. The bending moment M is a sum of Mx and My shown in FIG. 1. Also, the nugget is a rigid body.

The method is explained with the disk 31 of D in the diameter and t in the thickness shown in FIG. 3. As described, the disk 31 is loaded with the peel force Fz and the bending moment M (a sum of Mx and My shown in FIG. 1). While the external forces are exerted on the nugget 15 (d in diameter), the supporting condition at the circumference of the disk 31 is an actual condition over the spot welded structure. It is also noted that the nugget 15 is a rigid body. The condition at the circumference of the disk 31 is not the perfect arresting condition for no strain which is applied to Equations 1 and 2 but a variable condition for corresponding to the degree of strain about the nugget 15 of the spot welded structure, which will be described later in more detail. Moreover, the polar coordinates (r, $\theta z$) are concerned having their origin at the center of the nugget 15.

When the disk 31 is loaded with external forces, it bends thus producing internal strain and stress which are firstly calculated. The degree of bending of the elastodynamics on the disk 31 is calculated from:

$$\Delta\Delta w = 0 \quad (7)$$

$$\Delta = \frac{\partial^2}{\partial r^2} + \frac{1}{r}\frac{\partial}{\partial r} + \frac{1}{r^2}\frac{\partial^2}{\partial \theta^2}$$

It is then necessary to determine such a function of w (deflection along the z direction) that Equation 7 is satisfied. The deflection function for satisfying Equation 7 is commonly expressed by r and $\theta$ of a trigonometric function shown below as Equation 8.

$$w = w_0 + w_1 + \sum_{n=2}^{\infty} w_n \quad (8)$$

$$= f_0(r) + f_1(r)\cos\theta + \sum_{n=2}^{\infty} f_n(r)\cos n\theta +$$

$$g_1(r)\cos\theta + \sum_{n=2}^{\infty} g_n(r)\sin n\theta$$

-continued $$f_0(r) = A_o + B_0 r^2 + C_0 \ln r + D_0 r^2 \ln r$$

$$f_1(r) = A_1 r + B_1 r^3 + C_1 r^{-1} + D_1 r \ln r$$

$$f_n(r) = A_n r^n + B_n r^{-n} + C_n r^{n+2} + D_n r^{-n+2}$$

$$g_1(r) = A'_1 r + B'_1 r^3 + C'_1 r^{-1} + D'_1 r \ln r$$

$$g_n(r) = A'_n r^n + B'_n r^{-n} + C'_n r^{n+2} + D'_n r^{-n+2}$$

In Equation 8, An to Dn are 4(n+1) unknown factors determined by the boundary condition. When the factors are determined, Equation 8 is solved.

The factors are determined with the following two conditions.

(1) Condition for Having the Nugget as a Rigid Body

As its nugget 15 of a circular shape shown in FIG. 3 is rigidly deflected but not deformed, the deflection w and tilting $\delta w/\delta r$ of the disk is expressed at the nugget edge, r=d/2, by:

$$w_{r=d/2} = w_c + (d/2)(-\theta_{yc}\cos\theta + \theta_{xc}\sin\theta) \quad (9)$$

$$\left(\frac{\partial w}{\partial r}\right)_{r=d/2} = -\theta_{yc}\cos\theta + \theta_{xc}\sin\theta$$

where Wc, $\theta xc$, and $\theta yc$ are unknown factors which are determined from the condition below.

(2) Supporting Condition at the Circumference of Disk

It is essential at the circumference of the disk to match the supporting condition of an actual spot welded structure. Hence, the deflection wr=D/2 and tilting $\delta w/\delta r$ at the circumference (r=D/2) of the disk is calculated from:

$$w_{r=D/2} = \frac{1}{2}\alpha_{w0} + \sum_{n=1}^{\infty}\alpha_{wn}\cos n\theta + \sum_{n=1}^{\infty}\beta_{wn}\sin n\theta \quad (10)$$

$$\left(\frac{\partial w}{\partial r}\right)_{r=D/2} = \frac{1}{2}\alpha_{ws0} + \sum_{n=1}^{\infty}\alpha_{wsn}\cos n\theta + \sum_{n=1}^{\infty}\beta_{wsn}\sin n\theta$$

The right side of Equation 10 represents a deflection at the circumference of the disk shown in FIG. 3 and can be determined from the node deflection calculated by the spot welded structure FEM shell analyzing process. This process will be explained in more detail.

(i) As a circle of D in diameter has been defined about the nugget of interest, the discrete value of its node deflection (w, $\theta r$) is calculated by the FEM shell analyzing process where w is the out-of-plane deflection and $\theta r$ is the angle of tilting at the deflection w in a radial direction.

$$\theta_r = \left(\frac{\partial w}{\partial r}\right)_{r=D/2} \quad (11)$$

(ii) The circumferential distribution of the deflection (w, $\theta r$) is interpolated using a cubic cyclic spline interpolation function of the discrete values. For example, when the number of nodes qi in the interpolation function is nine, the spline interpolation function of the deflection w on the circumference of the circle is expressed by:

$$w(\theta)_{r=D/2} = \sum_{i=-2}^{5} a_i B_{i,4}(\theta) + \sum_{i=-2}^{-1} a_i B_{i+8,4}(\theta) + a_5 B_{-3,4}(\theta) \quad (12)$$

$B_{i,4}$ is determined from a recursion formula of cubic B spline.

$$B_{i,4}(\theta) = \frac{\theta - q_i}{q_{i+1} - q_i} B_{i,3}(\theta) + \frac{q_{i+4} - \theta}{q_{i+4} - q_{i+1}} B_{i+1,3}(\theta) \quad (13)$$

$$B_{i,1}(\theta) = 1 \, (q_i \le \theta < q_{i+1}),$$

$$0 \, (\theta < q_i, \theta \ge q_{i+1})$$

The coefficient $a_i$ in Equation 12 is determined so that $w(\theta)_{r=D/2}$ represents the node value at $\theta = q_i$.

The deflection $(\theta_r, (\theta)_{r=D/2})$ is also expressed by the spline interpolation function.

(iii) The interpolation functions are then converted to Fourier series, representing the boundary condition at the circumference of the disk as denoted at the right side of Equation 10. The factors in the Fourier series in Equation 10 is calculated from:

$$\alpha_{wn} = \frac{1}{\pi} \int_0^{2\pi} w(\theta)_{r=D/2} \cos n\theta \quad (14)$$

$$\alpha_{wsn} = \frac{1}{\pi} \int_0^{2\pi} \theta_r(\theta)_{r=D/2} \cos n\theta$$

$$\beta_{wn} = \frac{1}{\pi} \int_0^{2\pi} w(\theta)_{r=D/2} \cos n\theta$$

$$\beta_{wsn} = \frac{1}{\pi} \int_0^{2\pi} \theta_r(\theta)_{r=D/2} \cos n\theta$$

Using the boundary condition, the unknown constants in the deflection function of Equation 8 are determined.

From the deflection function, the force and moment in the cross section of the disk are calculated from:

$$M_r = -D_p \left[ M_{r0} + \sum_{n=1}^{\infty} M_{rfn} \cos n\theta + \sum_{n=1}^{\infty} M_{rgn} \sin n\theta \right] \quad (15)$$

$$M_\theta = -D_p \left[ M_{\theta 0} + \sum_{n=1}^{\infty} M_{\theta fn} \cos n\theta + \sum_{n=1}^{\infty} M_{\theta gn} \sin n\theta \right]$$

$$M_{r\theta} = (1-v) D_p \left[ \sum_{n=1}^{\infty} M_{r\theta fn} \sin n\theta + \sum_{n=1}^{\infty} M_{r\theta gn} \cos n\theta \right]$$

$$M_{r0} = \frac{d^2 f_0}{dr^2} + \frac{v}{r} \frac{df_0}{dr}$$

$$M_{rfi} = \frac{d^2 f_i}{dr^2} + \frac{v}{r} \left( \frac{df_i}{dr} - \frac{f_i}{r} i^2 \right) \quad (i \ge 1)$$

$$M_{rgi} = \frac{d^2 g_i}{dr^2} + \frac{v}{r} \left( \frac{dg_i}{dr} - \frac{g_i}{r} i^2 \right) \quad (i \ge 1)$$

$$M_{\theta 0} = v \frac{d^2 f_0}{dr^2} + \frac{1}{r} \frac{df_0}{dr}$$

$$M_{\theta fi} = v \frac{d^2 f_i}{dr^2} + \frac{1}{r} \left( \frac{df_i}{dr} - \frac{f_i}{r} i^2 \right) \quad (i \ge 1)$$

-continued $$M_{\theta gi} = v \frac{d^2 g_i}{dr^2} + \frac{1}{r} \left( \frac{dg_i}{dr} - \frac{g_i}{r} i^2 \right) \quad (i \ge 1)$$

$$M_{r\theta fi} = -\frac{i}{r} \left( \frac{df_i}{dr} - \frac{f_i}{r} \right) \quad (i \ge 1)$$

$$M_{rgi} = \frac{i}{r} \left( \frac{dg_i}{dr} - \frac{g_i}{r} \right) \quad (i \ge 1)$$

where Dp is the bending rigidity of the disk.

$$D_p = \frac{Et^3}{12(1-v)} \quad (16)$$

where E is the Young's modulus and $v$ is the Poisson's ratio.

Using the moment in the cross section, the stress on the disk is then calculated from:

$$\sigma_r = \frac{12 M_r z}{t^3} \quad (17)$$

$$\sigma_\theta = \frac{12 M_\theta z}{t^3}$$

$$\tau_{r\theta} = \frac{12 M_{r\theta} z}{t^3}$$

Equation 15 substitutes for Equation 17 (Z=t/2), then Equation 17 is arranged as follows:

$$\sigma_r = -D_p \frac{6}{t^2} \left[ M_{r0} + \sum_{n=1}^{\infty} M_{rfn} \cos n\theta + \sum_{n=1}^{\infty} M_{rgn} \sin n\theta \right]$$

$$\sigma_\theta = -D_p \frac{6}{t^2} \left[ M_{\theta 0} + \sum_{n=1}^{\infty} M_{\theta fn} \cos n\theta + \sum_{n=1}^{\infty} M_{\theta gn} \sin n\theta \right]$$

$$\tau_{r\theta} = (1-v) D_p \frac{6}{t^2} \left[ \sum_{n=1}^{\infty} M_{r\theta fn} \sin n\theta + \sum_{n=1}^{\infty} M_{r\theta gn} \cos n\theta \right]$$

Then, the balance between the inner force and the outer force along the x direction on the disk shown in FIG. 3 as well as the balance in the moment between the x direction and the y direction are concerned.

$$-\int_0^{2\pi} Q_r \left( \frac{d}{2} \right) d\theta = F_z \quad (18)$$

$$-\int_0^{2\pi} (M_{r\theta} \cos\theta - M_r \sin\theta) \left( \frac{d}{2} \right) d\theta - \int_0^{2\pi} Q_r \left( \frac{d}{2} \right)^2 \sin\theta d\theta = M_x$$

$$-\int_0^{2\pi} (M_{r\theta} \sin\theta + M_r \cos\theta) \left( \frac{d}{2} \right) d\theta + \int_0^{2\pi} Q_r \left( \frac{d}{2} \right)^2 \cos\theta d\theta = M_y$$

When the deflection function of Equation 8 is expressed by the coefficients An to Dn determined using the boundary condition and substituted in Equation 18, the constants $w_c$, $\theta_{cx}$, and $\theta_{cy}$ in Equation 9 are expressed by the peel load Fz and the bending moments Mx and My.

As a result, when the FEM shell analyzing process for the spot welded structure has been completed, all the unknown factors in Equation 8 are determined from the partial loads on the nugget and the node deflection on the circumference of the disk, D in diameter.

Although the nominal structural stress responsive to the peel load and the bending moment is hardly expressed by simple formulas such as Equations 1 and 2 in the method of the present invention, it can eliminate the troublesome step of determining the outer diameter D of a disk to an optimum in the actual measurement of a spot welded structure. Also, the method allows the degree of strain about the nugget of a spot welded structure to be expressed by the boundary condition, thus improving the accuracy of calculation of the nominal structural stress.

The method of the present invention is easily converted into an analyzing program which is then installed in the CAE system, hence permitting the ease of the estimation of the fatigue life of a spot welded structure.

Figure 23:
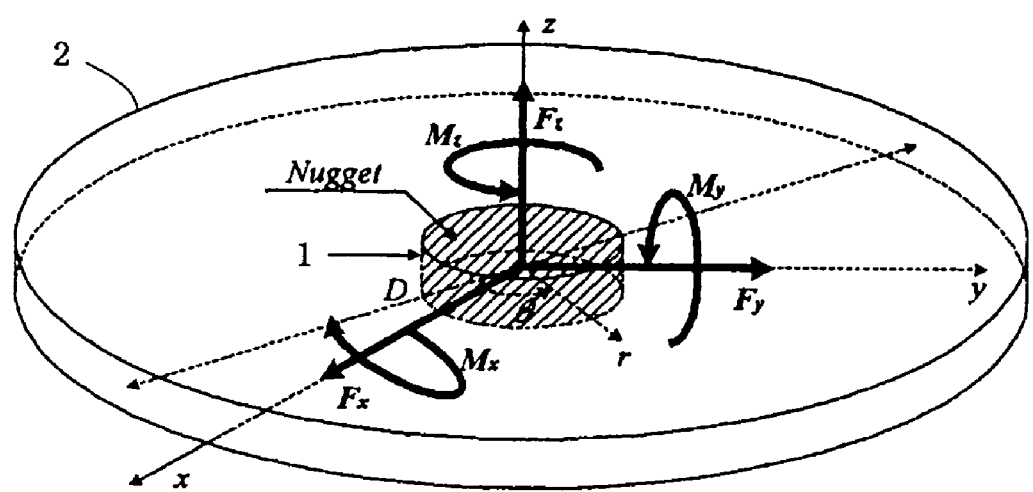
FIG. 23 is an explanatory view showing six partial forces exerted on the nugget for a fatigue life estimating method for a spot welded structure.

The procedure of calculating the nominal structure stress responsive to the shearing force and the torsional moment will be described referring to FIG. 23. This solution can be achieved from a plane stress theory of the elastodynamics. The solution is calculated from:

$$\Delta\Delta\phi = 0 \tag{19}$$

$$\Delta = \frac{\partial^2}{\partial r^2} + \frac{1}{r}\frac{\partial}{\partial r} + \frac{1}{r^2}\frac{\partial^2}{\partial \theta^2}$$

The stress function for satisfying the above equation is then expressed by:

$$\phi = a_0 \log r + b_0 r^2 + \frac{a_1}{2} r\theta \sin\theta - \frac{c_1}{2} r\theta \cos\theta + \tag{20}$$
$$(b_1 r^3 + a'_1 r^{-1} + b'_1 r\log r)\cos\theta + (d_1 r^3 + c'_1 r^{-1} + d'_1 r\log r)\sin\theta +$$
$$\sum_{n=2}^{\infty} (a_n r^n + b_n r^{n+2} + a'_n r^{-n} + b'_n r^{-n+2})\cos n\theta +$$
$$\sum_{n=2}^{\infty} (c_n r^n + d_n r^{n+2} + c'_n r^{-n} + d'_n r^{-n+2})\sin n\theta$$

The coefficients $a_0$ to $d'_n$ in Equation 20 are unknown factors which are determined by the boundary condition. The stress is then calculated using the stress function $\phi$ as expressed by:

$$\sigma_r = \frac{1}{r}\frac{\partial \phi}{\partial r} + \frac{1}{r^2}\frac{\partial^2 \phi}{\partial \theta^2} \tag{21}$$

$$\sigma_\theta = \frac{\partial^2 \phi}{\partial r^2}$$

$$\tau_{r\theta} = -\frac{\partial}{\partial r}\left(\frac{1}{r}\frac{\partial \phi}{\partial \theta}\right)$$

The relationship between the deflection and the deflection is then expressed by:

$$\varepsilon_r = \frac{\partial u}{\partial r} \tag{22}$$

$$\varepsilon_\theta = \frac{u}{r} + \frac{1}{r}\frac{\partial v}{\partial \theta}$$

$$\gamma_{r\theta} = \frac{1}{r}\frac{\partial u}{\partial \theta} + \frac{\partial v}{\partial r} - \frac{v}{r}$$

where u and v are the deflection along the directions of $\gamma$ and $\theta$ respectively. The relationship between the deflection and the deflection is calculated using the plane stress function as expressed by:

$$\varepsilon_r = \frac{1}{E}(\sigma_r - v\sigma_\theta) \tag{23}$$

$$\varepsilon_\theta = \frac{1}{E}(\sigma_\theta - v\sigma_r)$$

$$\gamma_{r\theta} = \frac{1}{G}\tau_{r\theta}$$

where E is the Young's modulus and G is the shearing elastic coefficient.

When the stress function of Equation 20 is substituted in Equation 21, the stress is then expressed by:

$$\sigma_r = a_0 r^{-2} + 2b_0 + \left(\frac{a_1}{r} + 2b_1 r - 2a'_1 r^{-3} + b'_1 r^{-1}\right)\cos\theta + \tag{24}$$
$$\left(\frac{c_1}{r} + 2d_1 r - 2c'_1 r^{-3} + d'_1 r^{-1}\right)\sin\theta +$$
$$\sum_{n=2}^{\infty} \left\{\begin{array}{l} a_n n(1-n)r^{n-2} + b_n(n+2-n^2)r^n - \\ a'_n n(1+n)r^{-n-2} + b'_n(-n+2-n^2)r^{-n} \end{array}\right\}\cos n\theta +$$
$$\sum_{n=2}^{\infty} \left\{\begin{array}{l} c_n n(1-n)r^{n-2} + d_n(n+2-n^2)r^n - \\ c'_n n(1+n)r^{-n-2} + d'_n(-n+2-n^2)r^{-n} \end{array}\right\}\sin n\theta$$

$$\sigma_\theta = -a_0 r^{-2} + 2_0 + (6b_1 r + 2a'_1 r^{-3} + b'_1 r^{-1})\cos\theta +$$
$$(6d_1 r + 2c'_1 r^{-3} + d'_1 r^{-1})\sin\theta +$$
$$\sum_{n=2}^{\infty} \left\{\begin{array}{l} a_n n(n-1)r^{n-2} + b_n(n+2)(n+1)r^n + \\ a'_n n(n+1)r^{-n-2} + b'_n(-n+2)(-n+1)r^{-n} \end{array}\right\}\cos n\theta +$$
$$\sum_{n=2}^{\infty} \left\{\begin{array}{l} c_n n(n-1)r^{n-2} + d_n(n+2)(n+1)r^n + \\ c'_n n(n+1)r^{-n-2} + d'_n(-n+2)(-n+1)r^{-n} \end{array}\right\}\sin n\theta$$

$$\tau_{r\theta} = (2b_1 r - 2a'_1 r^{-3} + b'_1 r^{-1})\sin\theta - (2d_1 r - 2c'_1 r^{-3} + d'_1 r^{-1})\cos\theta +$$
$$\sum_{n=2}^{\infty} \left\{\begin{array}{l} a_n n(n-1)r^{n-2} + b_n n(n+1)r^n - \\ a'_n n(n+1)r^{-n-2} - b'_n n(n-1)r^{-n} \end{array}\right\}\sin n\theta -$$
$$\sum_{n=2}^{\infty} \left\{\begin{array}{l} c_n n(n-1)r^{n-2} + d_n n(n+1)r^n - \\ c'_n n(n+1)r^{-n-2} - d'_n n(n-1)r^{-n} \end{array}\right\}\cos n\theta$$

Then, the solutions are substituted in the first and second statements of Equation 23 to determine the deflection ($\varepsilon_x$, $\varepsilon_y$). The deflection is then substituted in the first and second statements of Equation 22 for integration. As a result, the deflections u and v are given.

$$Eu = \tag{25}$$
$$-a_0(1+v)r^{-1} + 2b_0(1-v)r + \left\{\begin{array}{l} a_1 \log r + b_1(1-3v)r^2 + \\ a'_1(1+v)r^{-2} + b'_1(1-v)\log r \end{array}\right\}\cos\theta +$$
$$\left\{\begin{array}{l} c_1 \log r + d_1(1-3v)r^2 + \\ c'_1(1+v)r^{-2} + d'_1(1-v)\log r \end{array}\right\}\sin\theta +$$

$$\sum_{n=2}^{\infty}\left\{\begin{array}{l}-a_n n(1+v)r^{n-1}+b_n\{(2-n)-v(n+2)\}r^{n+1}+\\ a'_n n(1+v)r^{-n-1}+b'_n\{(2+n)-v(-n+2)\}r^{-n+1}\end{array}\right\}\cos n\theta +$$

$$\sum_{n=2}^{\infty}\left\{\begin{array}{l}-c_n n(1+v)r^{n-1}+d_n\{(2-n)-v(n+2)\}r^{n+1}+\\ c'_n n(1+v)r^{-n-1}+d'_n\{(2+n)-v(-n+2)\}r^{-n+1}\end{array}\right\}\sin n\theta +$$

$$Ef(\theta)$$

$$Ev = \left\{\begin{array}{l}-a_1(v+\log r)+b_1(5+v)r^2+\\ a'_1(1+v)r^{-2}+b'_1(1-v)(1-\log r)\end{array}\right\}\sin\theta -$$

$$\left\{\begin{array}{l}-c_1(v+\log r)+d_1(5+v)r^2+\\ c'_1(1+v)r^{-2}+d'_1(1-v)(1-\log r)\end{array}\right\}\sin\theta +$$

$$\sum_{n=2}^{\infty}\left\{\begin{array}{l}c_n n(1+v)r^{n-1}+d_n\{(n+4)+vn\}r^{n+1}+\\ c'_n n(1+v)r^{-n-1}+d'_n\{(n-4)+vn\}r^{-n+1}\end{array}\right\}\sin n\theta -$$

$$E\int f(\theta)d\theta + Eg(r)$$

where $f(\theta)$ is the unknown function of $\theta$ and $g(r)$ is the unknown function of $r$. When the deflection of Equation 25 is substituted in the third statement of Equation 22, the shearing deflection is given. When the same is substituted in the third statement of Equation 23, the shearing stress is calculated. As the shearing stress is equal to the third statement of Equation 24, the two unknown functions $f(\theta)$ and $g(r)$ are expressed by:

$$f(\theta) = H\sin\theta + K\cos\theta \tag{26}$$

$$g(r)v = -\frac{a'_0}{2Gr} + Fr$$

where H, K, and F are the unknown constants.

The boundary condition at the edge of the nugget ($r=d/2$) is thus expressed by:

$$u_{r=d/2}=u_{xc}\cos\theta+u_{yc}\sin\theta\ v_{r=d/2}=-u_{xc}\sin\theta+u_{yc}\cos\theta+\theta_c b \tag{27}$$

where $u_{xc}$, $u_{yc}$, and $\theta_c$ are the constants determined by the conditions described below. As the nugget is a rigid body, the distribution along the circumferential direction of the deflection (u, v) is calculated from Equation 27.

When $r=D/2$, the deflection is expressed by:

$$u_{r=D/2} = \frac{1}{2}\alpha_{O u 0} + \sum_{n=1}^{\infty}\alpha_{Oun}\cos n\theta + \sum_{n=1}^{\infty}\beta_{Oun}\sin n\theta \tag{28}$$

$$v_{r=D/2} = \sum_{n=1}^{\infty}\alpha_{Ovn}\sin n\theta + \frac{1}{2}\beta_{Ov0} + \sum_{n=1}^{\infty}\beta_{Ovn}\cos n\theta$$

The right side of Equation 27 is the deflection at the circumference of the disk which can be expressed by the node deflection determined by the FEM shell analyzing process. More particularly, the deflection is calculated by the following steps.

(1) As a circle of D in diameter has been defined about the nugget of interest, the discrete value of the node deflection (u, v) determined by the FEM shell analyzing process is calculated.

(2) The circumferential distribution of the deflection (u, v) is interpolated using a cubic cyclic spline interpolation function of the discrete values. For example, when the number of nodes $q_i$ in the interpolation function is nine, the spline interpolation function of the deflection u on the circumference of the circle is expressed by:

$$u(\theta)_{r=D/2} = \sum_{i=-2}^{5} a_i B_{i,4}(\theta) + \sum_{i=-2}^{-1} a_i B_{i+8,4}(\theta) + a_5 B_{-3,4}(\theta) \tag{29}$$

$B_{i,4}(\theta)$ is determined from a recursion formula of cubic B spline.

$$B_{i,4}(\theta) = \frac{\theta - q_i}{q_{i+1} - q_i}B_{i,3}(\theta) + \frac{q_{i+4} - \theta}{q_{i+4} - q_{i+1}}B_{i+1,3}(\theta) \tag{30}$$

$$B_{i,1}(\theta) = 1(q_i \leq \theta < q_{i+1}),$$

$$0(\theta < q_i, \theta \geq q_{i+1})$$

The coefficient $\alpha_i$ in Equation 29 is determined so that $u(\theta)_{r=D/2}$ represents the node value at $\theta=q_i$.

The deflection $v(\theta)_{r=D/2}$ is also expressed by the spline interpolation function.

(3) The interpolation functions are then converted to Fourier series, representing the boundary condition.

The constants $u_{xc}$, $u_{yc}$, and $\theta_c$ in Equation 27 are calculated by balancing between the partial loads exerted on the nugget and the distribution of the stress about the nugget. This is expressed by:

$$F_x + \int_0^{2\pi}(\sigma_r\cos\theta - \tau_{r\theta}\sin\theta)bd\theta = 0 \tag{31}$$

$$F_y + \int_0^{2\pi}(\sigma_r\sin\theta + \tau_{r\theta}\cos\theta)bd\theta = 0$$

$$M_z + \int_0^{2\pi} b\tau_{r\theta}bd\theta = 0$$

Using the FEM shell analyzing process for a spot welded structure, the unknown coefficients in Equation 20 are determined from the partial loads exerted on the nugget and the node deflection on the circumference of the circle, D in diameter, about the nugget. As a result, the deflection field and the stress field about the nugget are calculated.

Then, the nominal structural stress under composite loads will be described.

Figure 22:
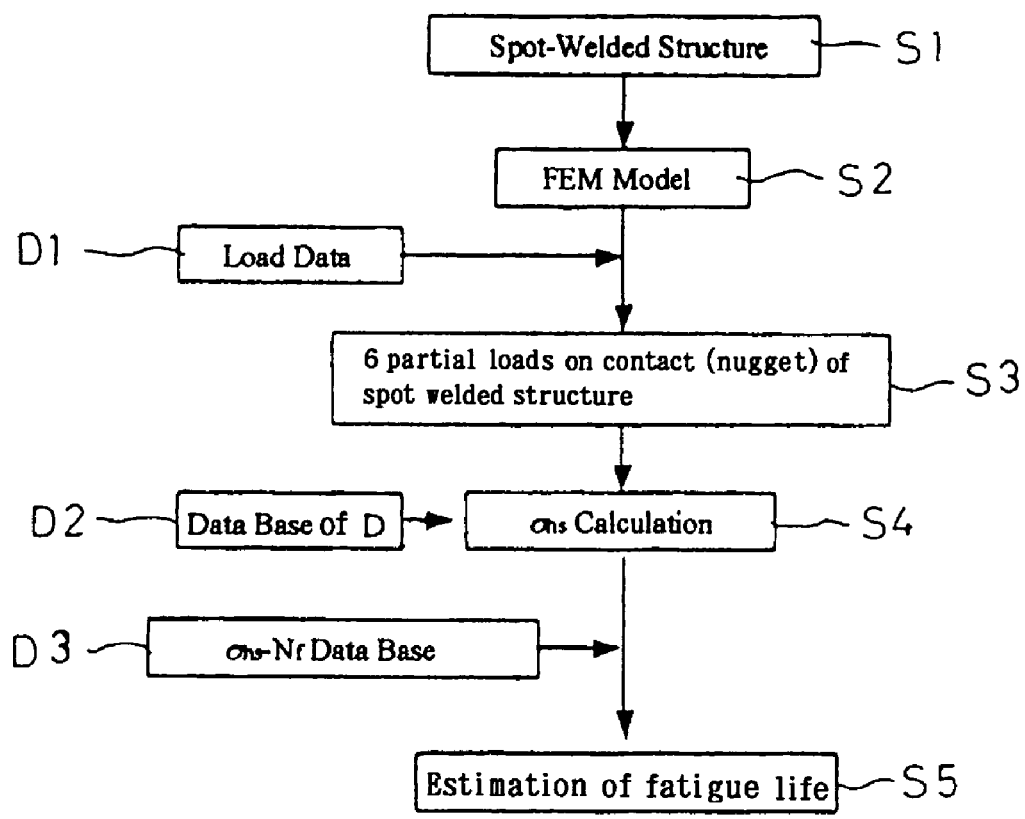
FIG. 22 is a flowchart showing a conventional fatigue life estimating method for a spot welded structure.

Referring to FIG. 22, when the peel load, the bending moment, the shear load, and the torsional moment are loaded at one time, the nominal structural stress is a maximum main stress at the edge of the nugget which acts as a fatigue strength parameter and is expressed by:

$$\sigma_{p1}, \sigma_{p2} = \frac{(\sigma_{rsum} + \sigma_{\theta sum}) \pm \sqrt{(\sigma_{rsum} - \sigma_{\theta sum})^2 + 4\tau_{r\theta sum}^2}}{2} \tag{32}$$

where $\sigma_{rsum}$, $\sigma_{\theta sum}$, and $\tau_{r\theta sum}$ are the combinations of analyzed results of the partial loads.

For confirming the effectiveness of the present invention, the nominal structural stress on the nugget 15 in the LP model 11 shown in FIG. 1. More specifically, the LP model 11 is prepared as a three-dimensional detailed solid model for examining the accuracy of the solution and subjected to the finite element method analyzing process for calculating the nominal structural stress. In common, each analysis of the vehicle bodies employs not such detailed solid models but shell models which are rather low in the load of calculation.

Example 1

Figure 5:
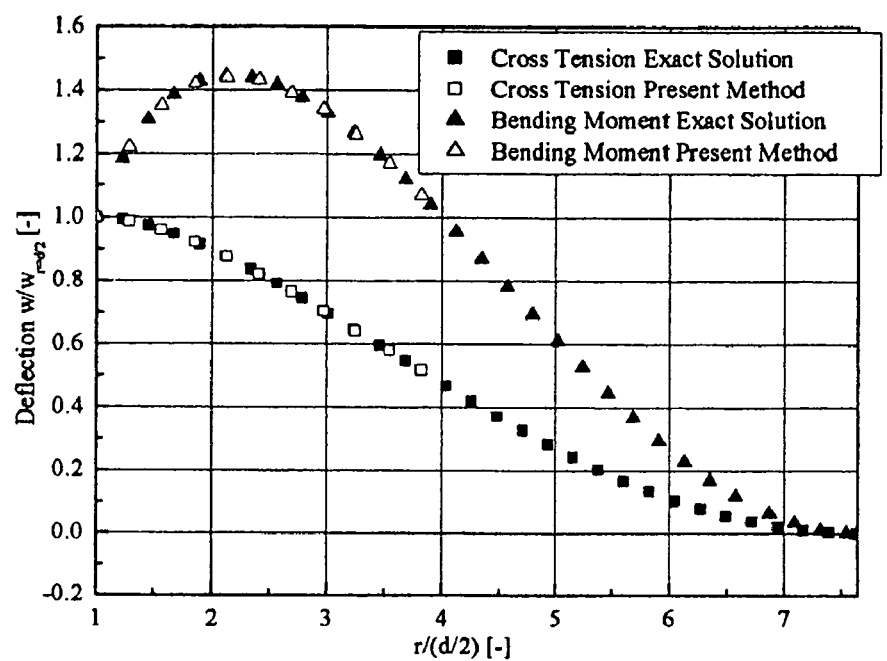
FIG. 5 is a graph showing comparison in the distribution of deflection between the method of the present invention and an exact solution when the peel load and the bending moment are exerted separately.

Prior to its application to the spot welded structure, the solution from the method of this embodiment is examined through comparing with the exact solution from the distribution of deflection, as shown in FIG. 5, where the disk shown in FIG. 3 is perfectly arrested at the circumference for no deflection and loaded with the peel load and the bending moment separately.

As apparent, the solution from the method is similar to the exact solution as based on the circumferential condition (the right side of Equation 6) determined by the deflection and the tilting at the intermediate of the disk (the peel load: r=3.82 (d/2), the bending moment: r=3.82 (d/2)).

Figure 6:
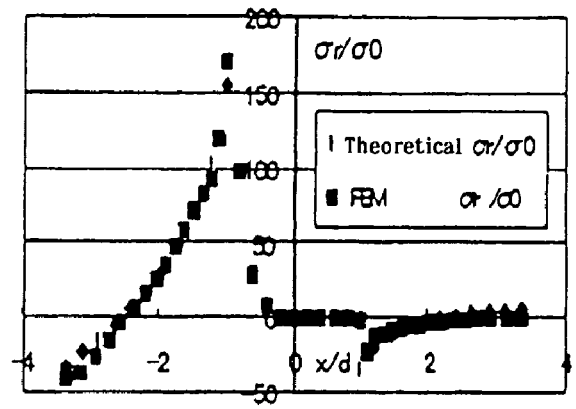
FIG. 6 illustrates comparison in the distribution of stress σr along the x axis extending across the center of the nugget between the fatigue life estimating method for a spot welded structure of the present invention and an FEM solid solution when loaded in the directions θx and θy shown in FIG. 1, FIGS. 6a and 6b being the distribution of stress σr on LP#90#90 and LP#45#90 respectively.
Figure 6:
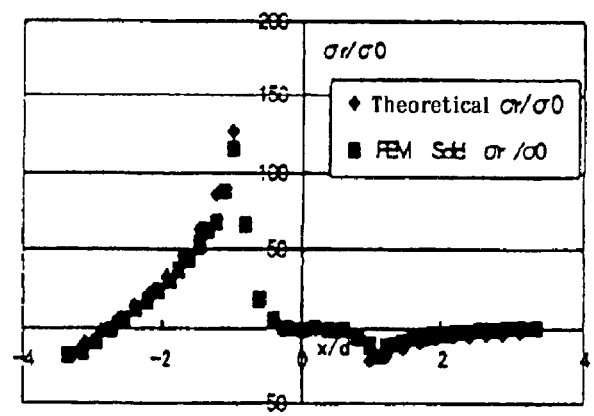

FIGS. 6a and 6b illustrate comparison between the distribution of the stress $\sigma_n$, calculated by the method of the present invention, along the x direction extending across the center of the nugget 15 and its counterpart from the FEM solid solution. LP#θx and θy represent the loads exerted in the θx and θy directions respectively shown in FIG. 1. FIG. 6a illustrates when LP#90#90 while FIG. 6b illustrates when LP#45#60. The two profiles are similar in either case.

Figure 7:
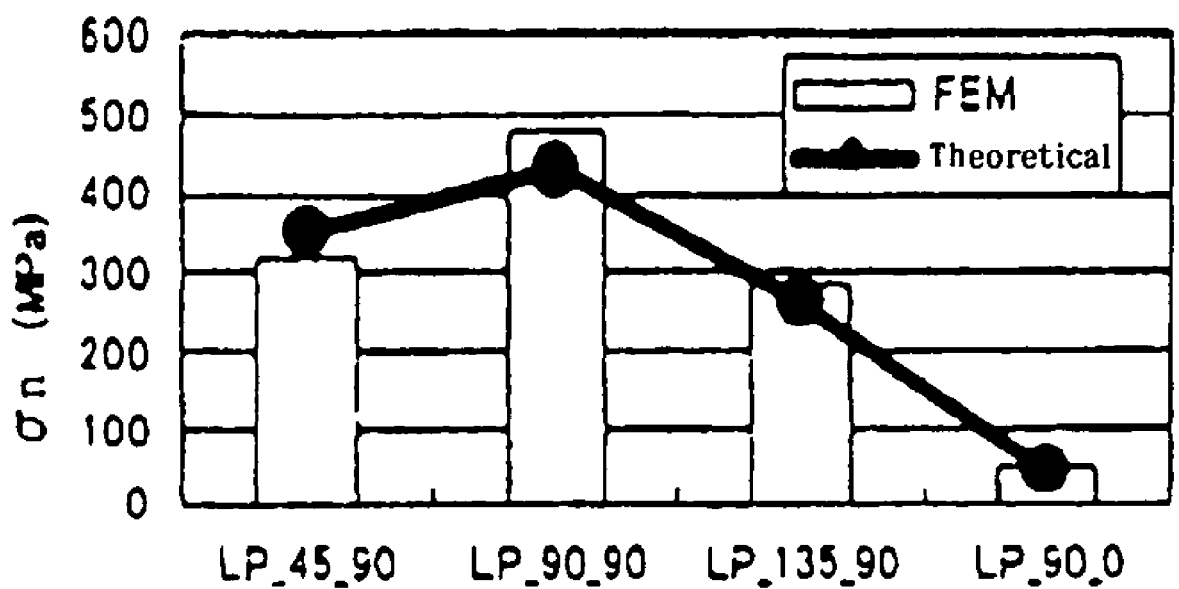
FIG. 7 is a graph showing the nominal structural stress on the nugget calculated by the fatigue life estimating method for a spot welded structure according to the method of the present invention.

FIG. 7 illustrates a profile of the nominal structural stress on the nugget calculated by the method of the present invention. In every loading case, the nominal structural stress calculated by the method of the present invention is similar to that of the solid model FEM solution. It is hence apparent that the nominal structural stress calculated by the method of the present invention is highly accurate as the parameter for estimating the fatigue life. It would be understood that the spot welded structure is not limited to the LP model 11 employed in this embodiment but may be any structure consisting of at least two or more pieces joined to each other by spot welding.

Example 2

Figure 8:
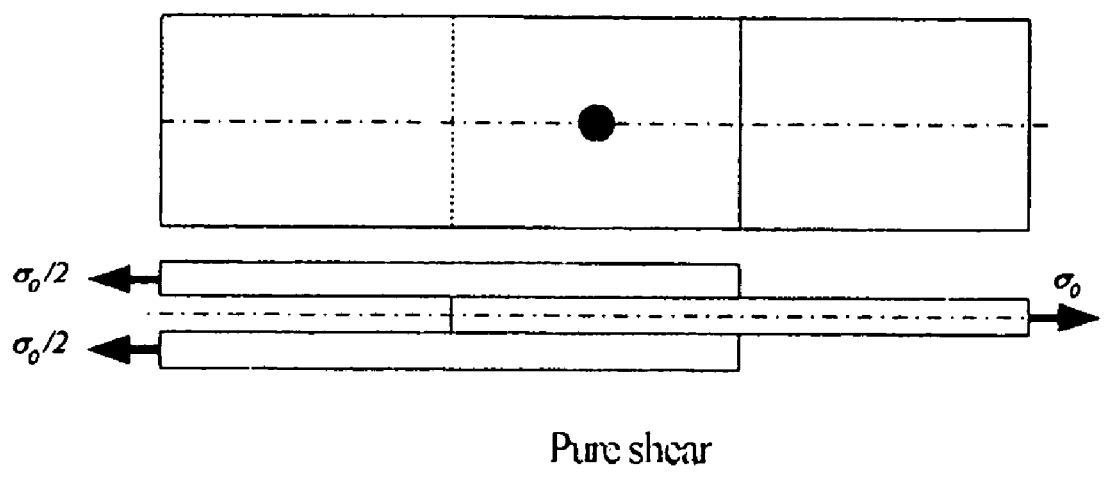
FIG. 8 illustrates a tensile shearing force exerted on a spot welded structure consisting of three flat four-sided strips joined together at one contact by spot welding for the method of the present invention.

While the nominal structural stress is calculated responsive to the peel load or the bending moment in Example 1, Example 2 is a case that the shear load is dominant as the partial load. It is typically assumed that the shear load is exerted on a test piece composed of three equal thickness strips joined together at one contact by spot welding (FIG. 8).

Figure 9:
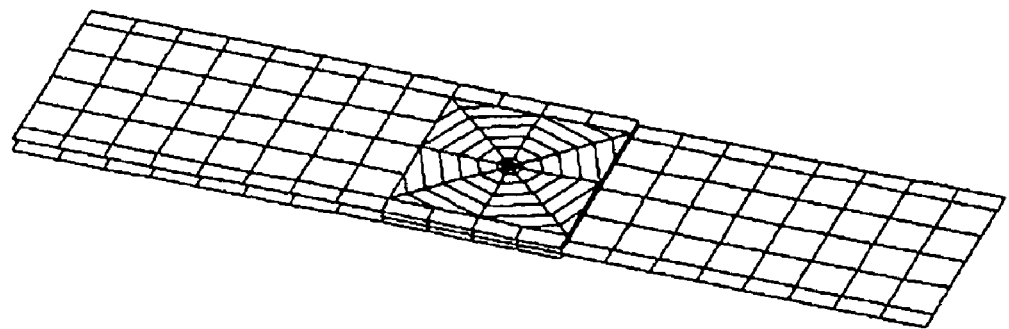
FIG. 9 is a view of an FEM shell analyzing model consisting of three spot welded plates for the method of the present invention.

Firstly, the finite element method shell analyzing process is carried out for acquiring the node deflection used as the boundary condition. FIG. 9 illustrates an FEM shell analyzing model composed of three spot welded strips. As the model is expressed by a grating pattern of small square segments, its center square portion about the nugget is designated having each side arranged equal to the lap length, which is divided radially by two at the nugget, by four at the other area than the nugget, and circumferentially by eight. The nugget includes bar elements arranged radially and extending along one side of the shell element. The two, upper and lower, strips are joined to each other at the center of the nugget by a beam element which is identical in the rigidity to the nugget area. The FEM solver is then subjected to the linear elastic analyzing process with the use of COSMOS/M.

The procedure of calculating the distribution of the stress about the nugget by the theory of the method will be described in conjunction with the shell analyzing model shown in FIG. 9.

(1) The shell model shown in FIG. 9 is prepared and subjected to the FEM analyzing process.

(2) The partial loads exerted on the nugget and the deflection (u, v) at eight node points on the circle, D in diameter, along the radial direction and the circumferential direction are determined from the result of the analyzing process carried out at the step (1).

(3) The distribution of the deflection (u, v) at the node points along the circumferential direction determined at the step (1) is interpolated with a cubic cyclic spline interpolation function. The result is converted to a Fourier series which is designated as the boundary condition on the circumference of the disk shown in FIG. 23.

(4) The distribution of the stress about the nugget is calculated by the theory of the embodiment under the boundary condition determined at the step (3).

Figure 10:
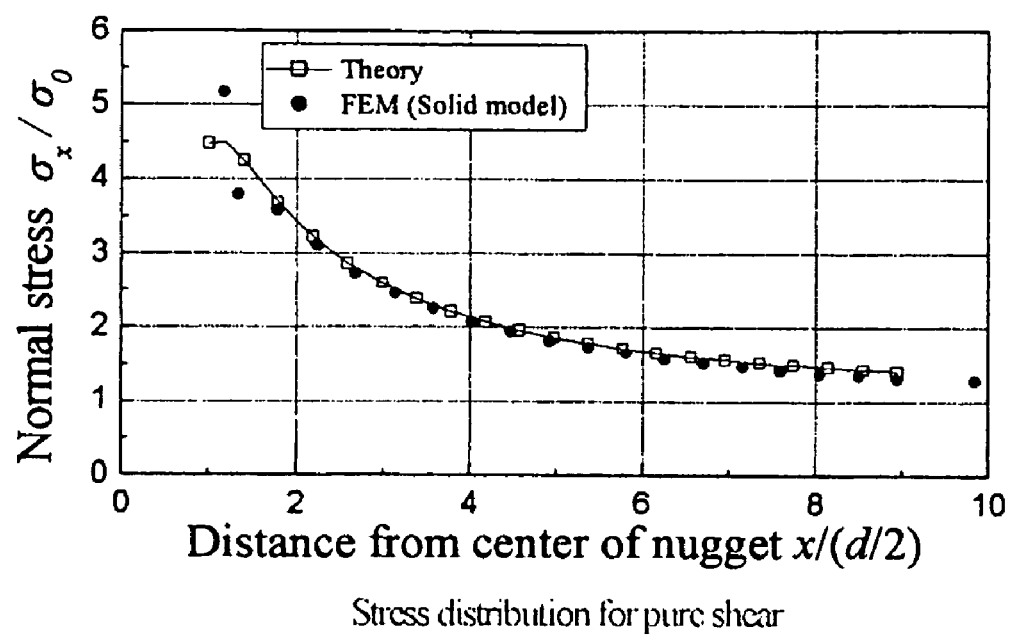
FIG. 10 illustrates a distribution of the stress on the spot welded structure consisting of three equal thickness strips joined together at one contact by spot welding according to the method of the present invention.
Figure 24:
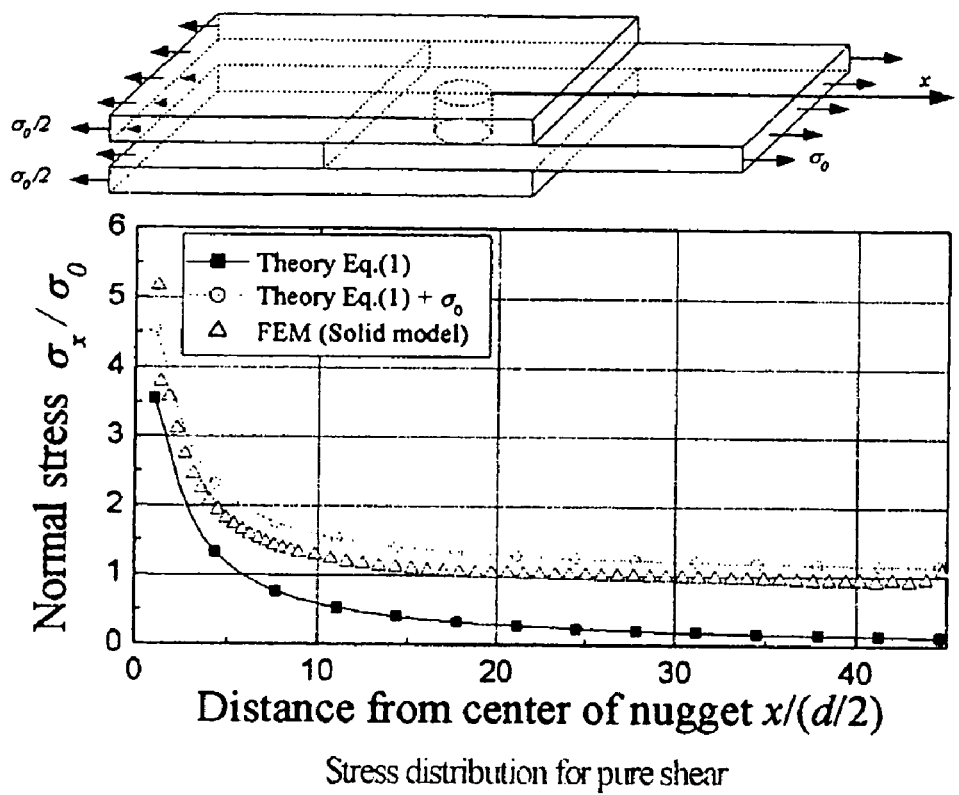
FIG. 24 illustrates a distribution of the stress on three equal thickness plates joined at one contact by spot welding for the method of the present invention.
Figure 25:
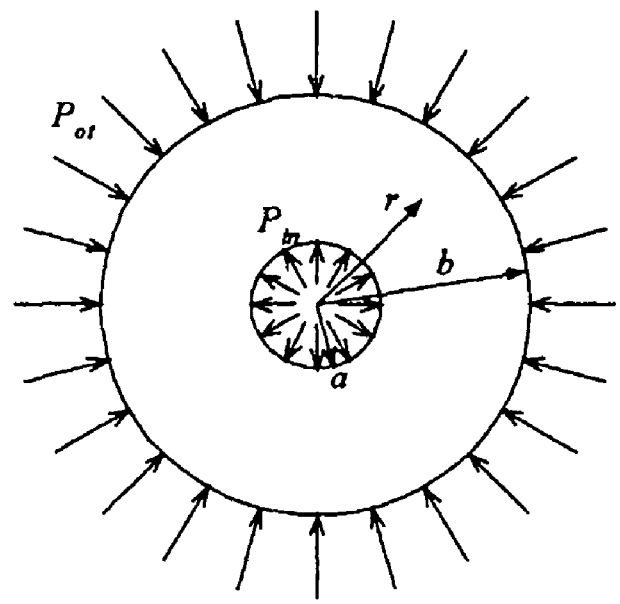
FIG. 25 illustrates a distribution of the stress on a doughnut shaped disk urged with outer and inner loads.
Figure 26:
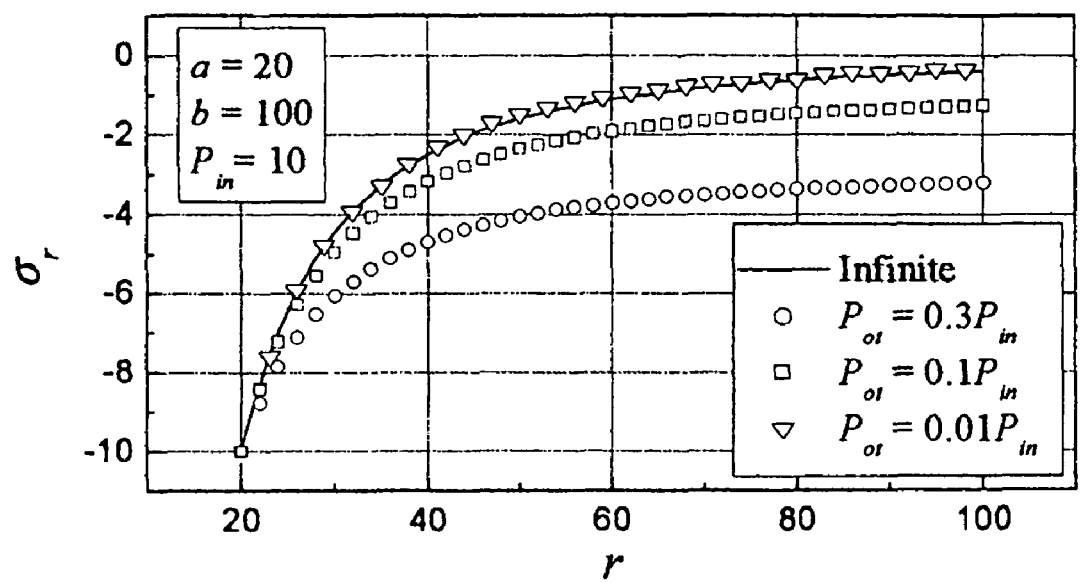
FIG. 26 illustrates comparison between the doughnut shaped disk and an infinite plate having an opening arranged equal in diameter to the inner hole of the doughnut disk.

A profile of the resultant distribution is shown in FIG. 10. The distribution of the stress along the center axis on the outer surface of the center strip of the three-strip spot welded assembly is shown as compared with the result of the FEM solid analyzing process. The conventional theory shown in FIG. 24 allows the stress to be decayed to zero as the point departs further from the nugget and its profile is dissimilar to the result of the FEM solid analyzing process. The method of the embodiment is similar in the profile of the distribution to the FEM solid analyzing process.

Example 3

Figure 11:
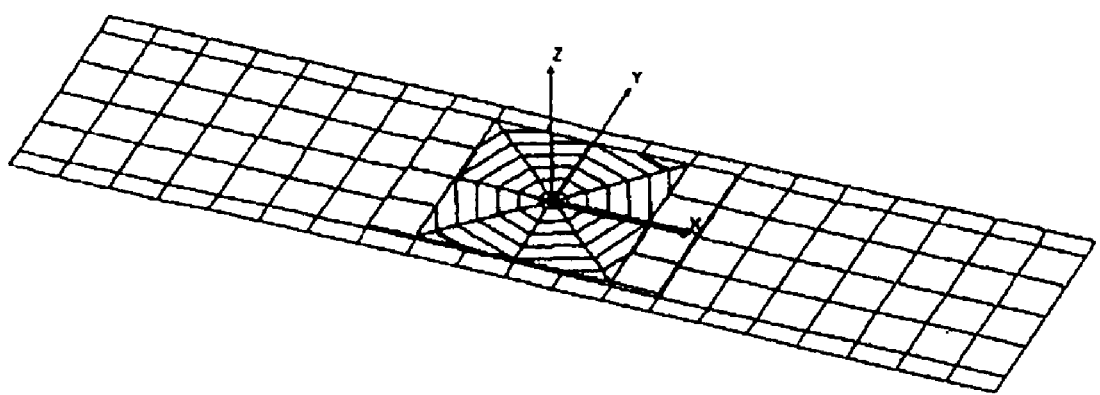
FIG. 11 is a view of an analyzing model composed of shell elements for the method of the present invention.
Figure 12:
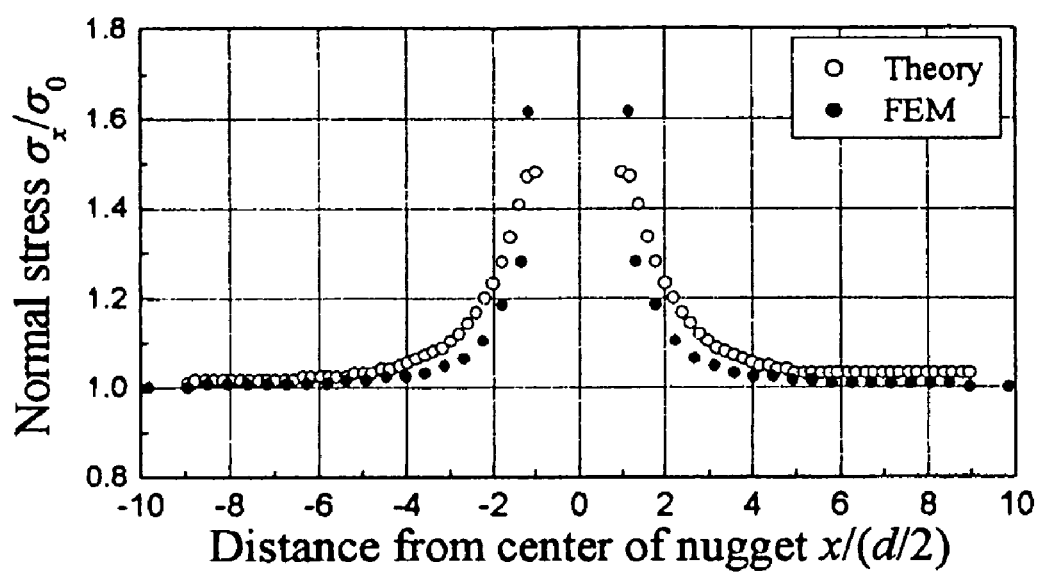
FIG. 12 illustrates a distribution of the stress on bracketed flat plates according to the method of the present invention.
Figure 27:
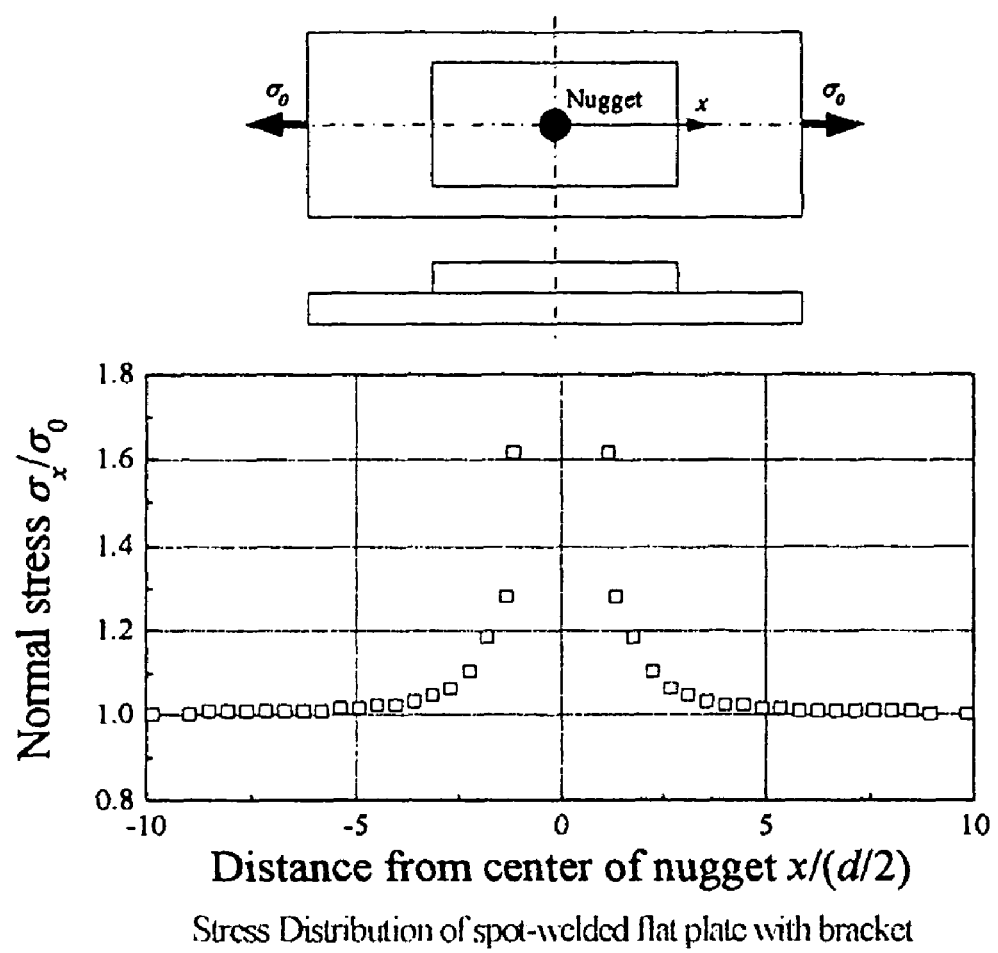
FIG. 27 illustrates a distribution of the stress on racketed plat plates for the method of the present invention.

Using a two, large and small, flat plates joined together by spot welding as shown in FIG. 27, the stress vertical to the loading direction is measured in response to a uniform tensile force $\sigma_o$ loaded at both sides. The procedure starts with preparing the analyzing model with shell elements as shown in FIG. 11 and calculating the distribution of the stress at the node points or vertices of an octagonal shape about the nugget. The resultant distribution is shown in FIG. 12. The distribution of the stress calculated by the method of the embodiment is favorably more similar to that of the FEM solid analyzing process than by the conventional method.

Example 4

Figure 13:
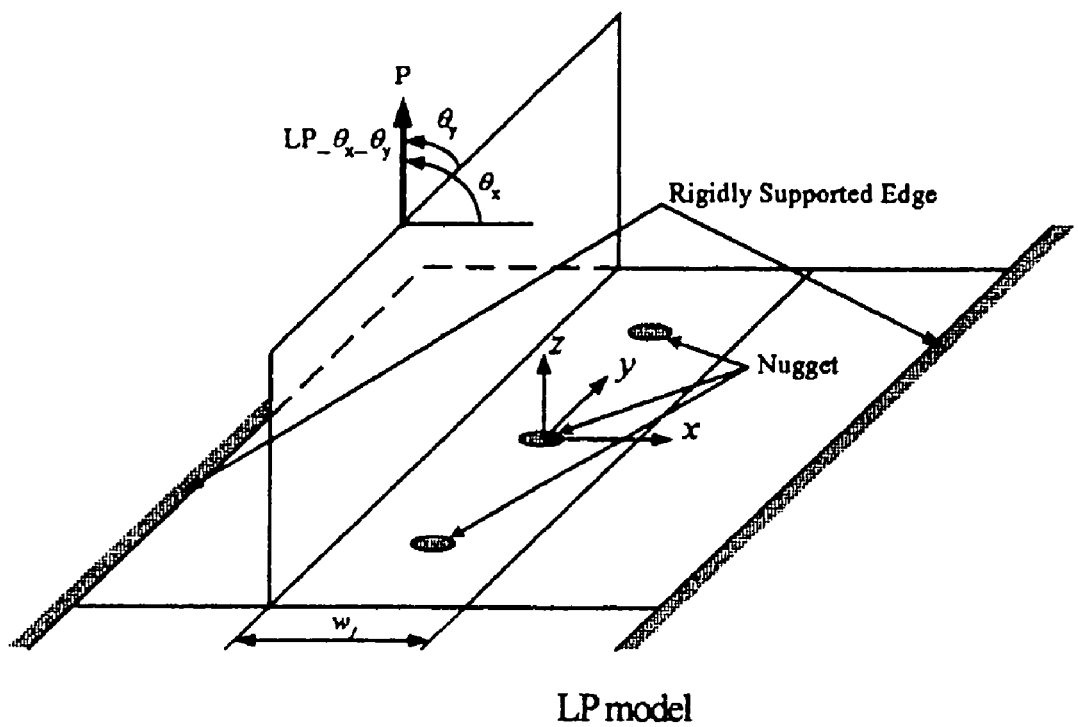
FIG. 13 illustrates a part of the L channel in the FEM shell analyzing model for the method of the present invention.

An LP model shown in FIG. 13 is now provided as the spot welded structure. The model consists of a flat plate and an L channel joined together at three contacts by spot welding. While the flat plate is not arrested at both sides, the L channel is urged at its upper end with a load P in various directions. When the load P is exerted in the θx and θy directions, it is expressed by LP_θx_θy. The L channel is 15 mm in the flange length and 135 in the overall length while the flat plate is 45 mm in the width. While the spot welding pitch is 45 mm, the thickness of both the components is 0.8 mm.

Figure 14:
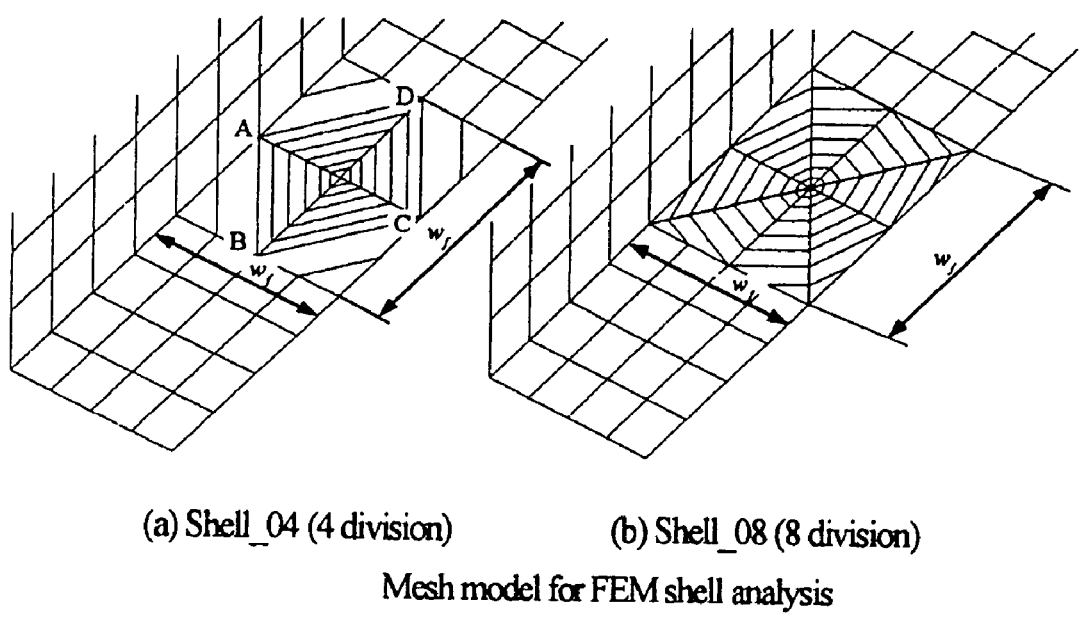
FIG. 14 illustrates modifications of the shell analyzing model for the method of the present invention.

FIG. 14 illustrates a part of the L channel of the FEM shell analyzing model. The model is denoted by a rough grating pattern of segments while the nugget and its adjacent area are expressed by a square having one side arranged equal to the flange width $w_f$. The nugget is divided radially by two while the other area than the nugget in the square is divided radially by four. The square is also divided circumferentially by four and by eight to develop a Shell_04 and a Shell_08 respectively. The nugget includes bar elements arranged radially and extending along one side of the shell element. The two, upper and lower, components are joined to each other at the center of the nugget by a beam element which is identical in the rigidity to the nugget area.

Figure 15:
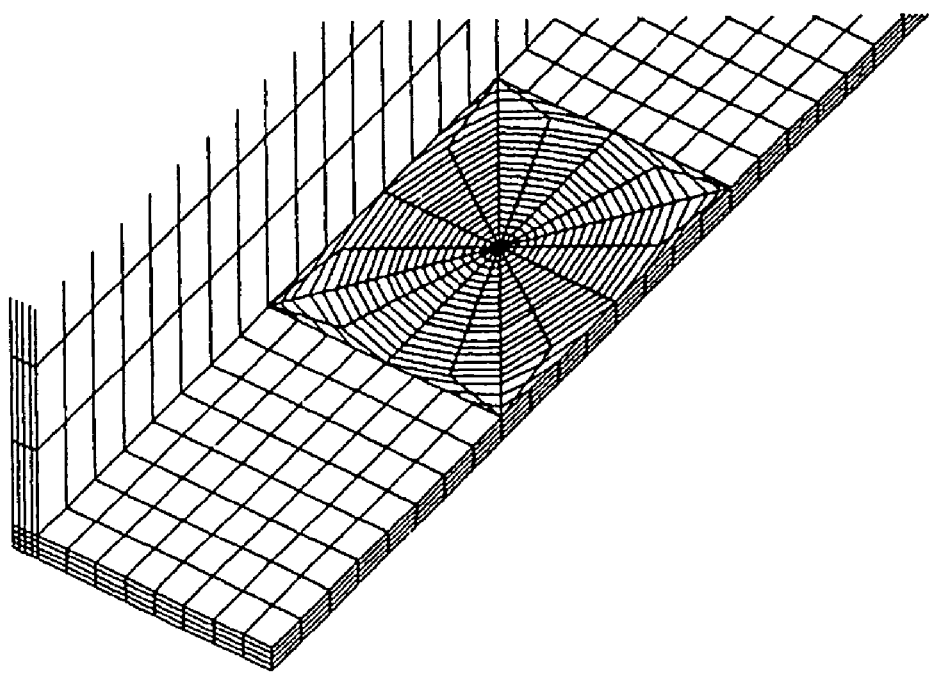
FIG. 15 illustrates a part of the L channel in an FEM solid model for cubic elastic analyzing process to examine the accuracy of solution for the method of the present invention.

FIG. 15 illustrates a part of the L channel of a cubic elastic analyzing FEM solid model prepared for examining the accuracy of the result of the method of the embodiment. The model is divided thickness wisely by four while the nugget is divided into smaller segments. The flat plate of the model is also denoted by the same. The loading condition (LP_θx_θy) and the arresting condition for no deflection are as shown in FIG. 13.

The procedure of the method calculating the distribution of the stress about the nugget will be described in conjunction with the shell analyzing model Shell_04 shown in FIG. 14a.

(1) The shell model shown in FIG. 14a is prepared and subjected to the FEM analyzing process.

(2) The deflection and tilting at the nodes (four points A, B, C, and D) where a polygon and a square are intersected is calculated from the measurements along the radial lines (two lines AC and BD shown in FIG. 14a), which extend from the center of the nugget, in the FEM analyzing process carried out at the step (1).

(3) The circumferential distribution of the stress is then interpolated with the deflection and tilting at the four nodes (using Equation 12) and converted into a Fourier series (Equation 10) which is regarded as the boundary condition at the circumference of the disk shown in FIG. 3.

(4) The partial loads exerted on the nugget of interest are calculated from the FEM shell analyzing process at the step (1). The peel load Fx and the bending moments Mx and My of the partial loads are substituted in Equation 9.

(5) The distribution of the stress about the nugget responsive to the peel load and the bending moment is then calculated at D=$w_f$ under the boundary conditions and the loading condition determined by the steps (3) and (4).

(6) The distribution of the stress responsive to the shear loads (Fx, Fy) and the torsional force Mz over the nugget is also calculated by the same steps (2) to (5).

(7) The stress responsive to the composite loads or the nominal structural stress is calculated from a combination of the results determined by the two steps (5) and (6) using Equation 32.

Figure 16:
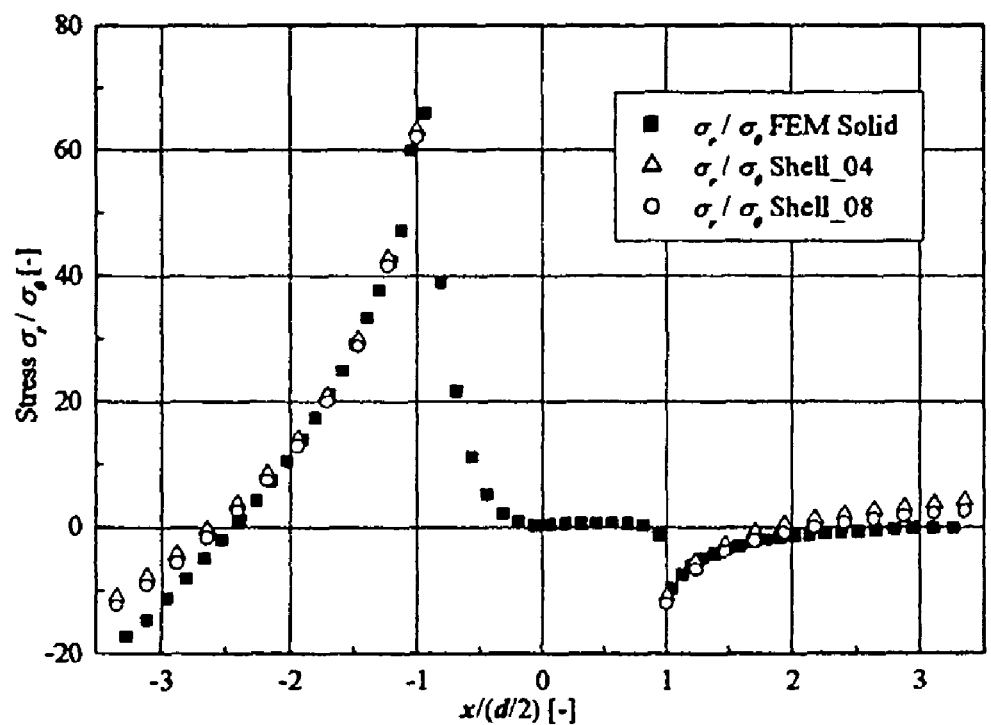
FIG. 16 illustrates a distribution of the stress according to the method of the present invention.

A profile of the resultant distribution of the stress is shown in FIG. 16. The profile exhibits comparison in the distribution of the stress $\sigma_r$ along the x direction on the nugget of the L channel in response to the loading force LP_90_90 between the two shell analyzing models Shell_04 and Shell_08. As apparent, the two models are not significantly different while the Shell_04 model designated by a rough grating pattern is similar to the FEM solid solution and its stress profile is favorable. The description below will hence be based on Shell_04 model. Denoted by $\sigma_o$ in the profile is an average stress determined through dividing the loading force by the involving area of the upper surface of the L channel.

Figure 17:
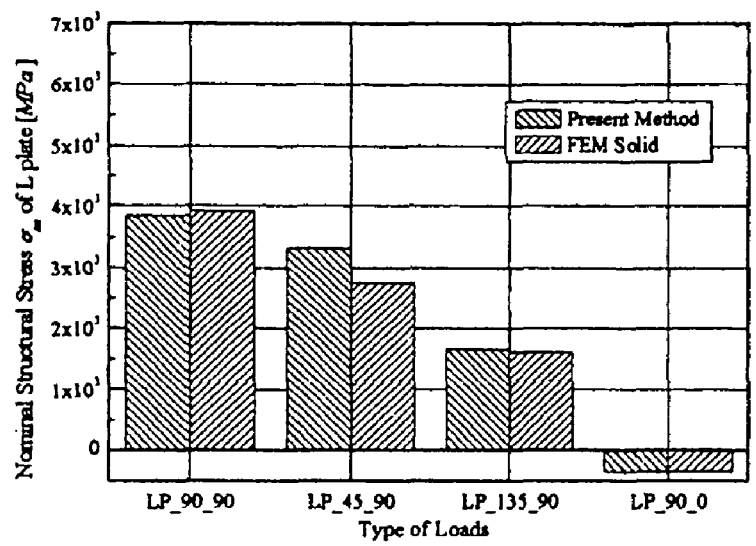
FIG. 17 is profiles of the nominal structural stress according to the method of the present invention.
Figure 17:
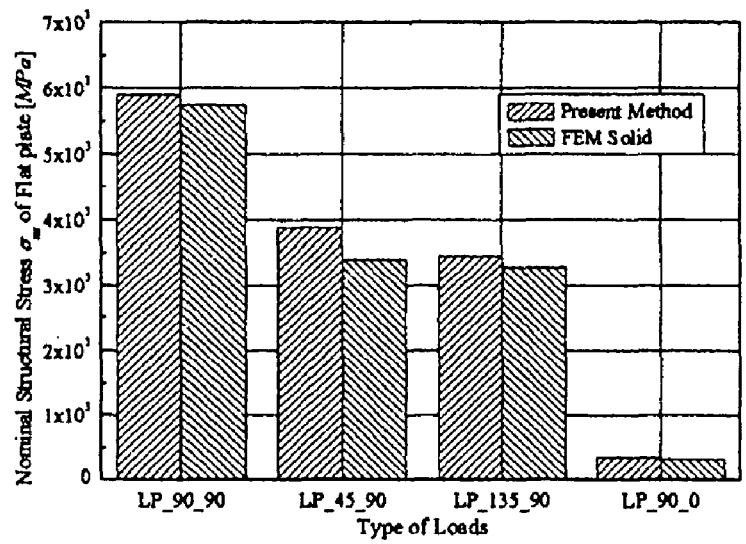

FIG. 17 illustrates comparison in the nominal structural stress between the method and the FEM solid analyzing process, where the result is favorably similar at any level of the loading force.

Figure 18:
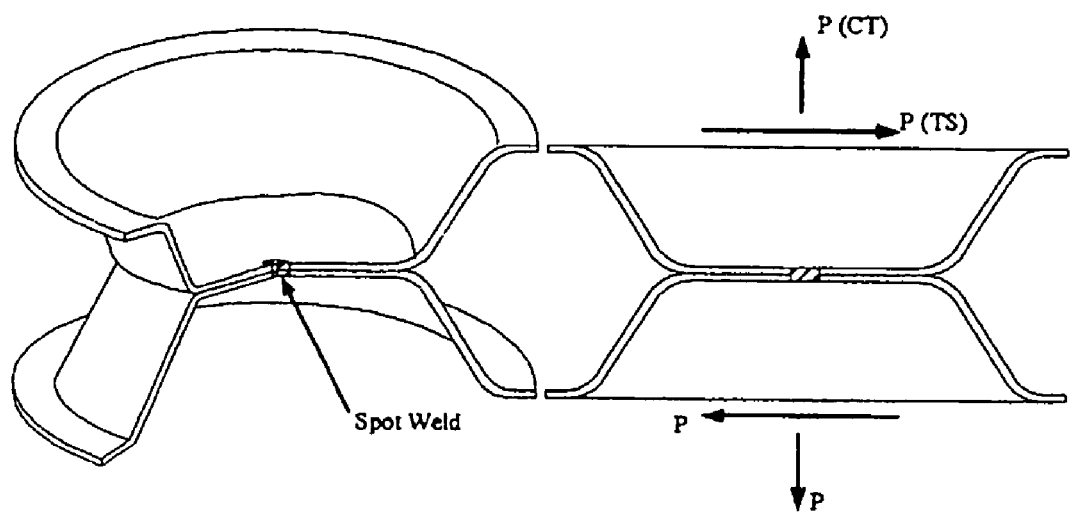
FIG. 18 illustrates a DC test piece for conducting a variety of composite load fatigue tests for the method of the present invention.
Figure 19:
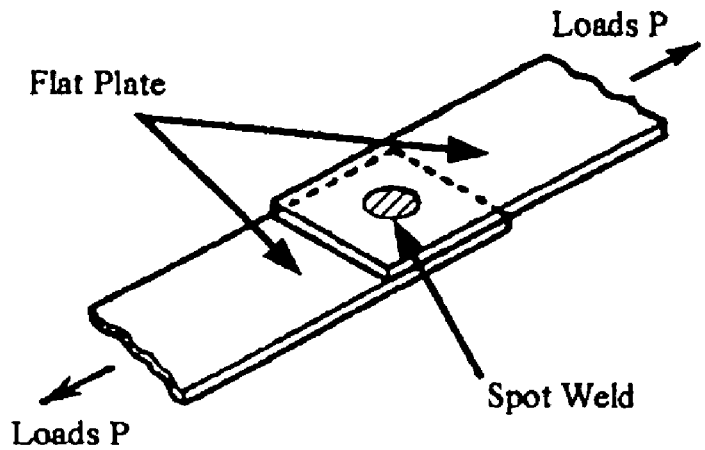
FIG. 19 illustrates a tensile shear (TS) test piece and a cross tension (CT) test piece as the typical spot welding fatigue test pieces for the method of the present invention.
Figure 19:
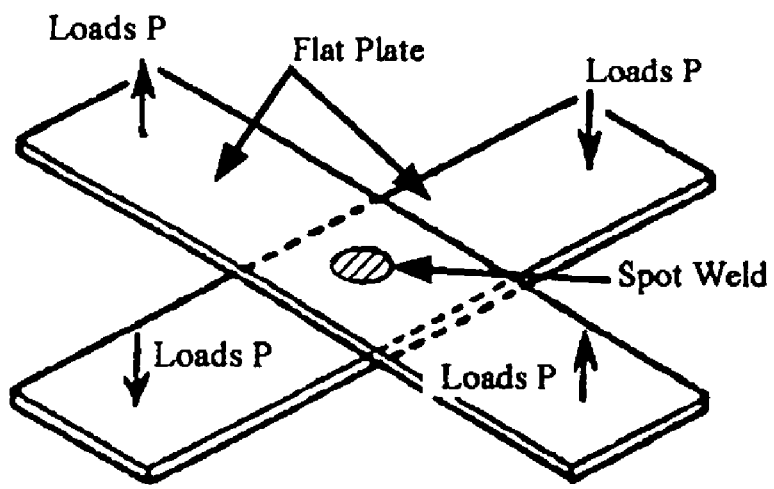

FIG. 18 illustrates a DC test piece (a pair of opposite cup-shaped components spot welded at a single contact) which is designed by Gieke, Hahn for permitting a variety of composite load fatigue tests to be conducted with one test piece. FIG. 19 illustrates a tensile shear (TS) test piece and a cross tension (CT) test piece used in a typical spot welding fatigue test.

Figure 20:
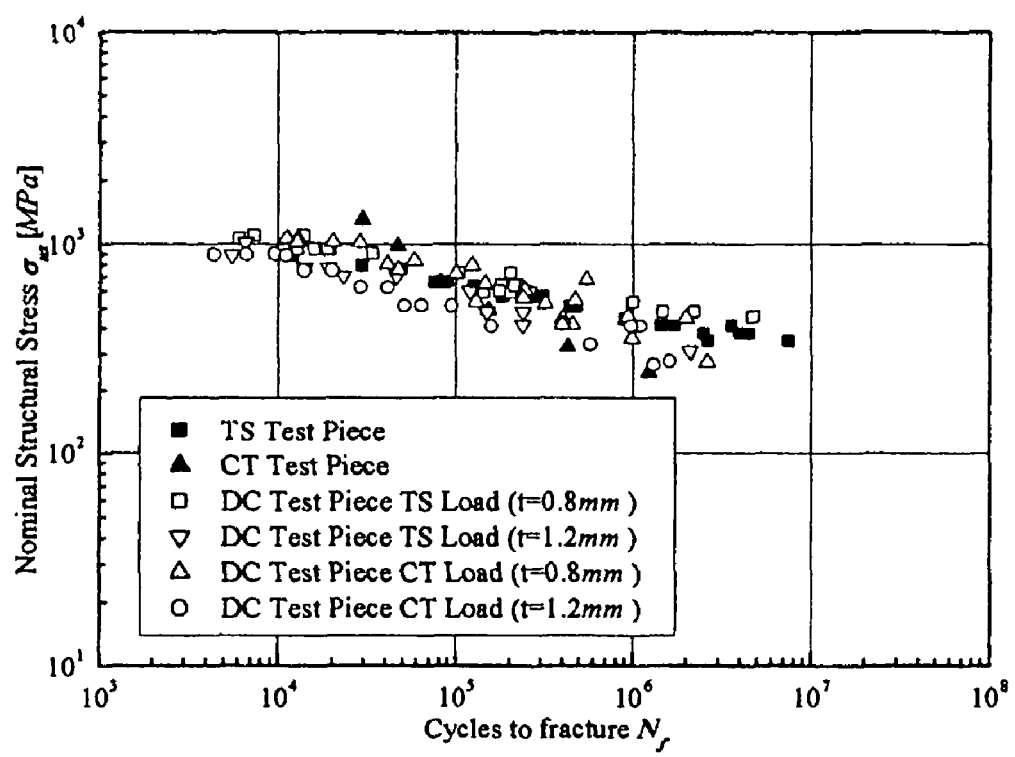
FIG. 20 is profiles of the nominal structural stress as fatigue test data on the test pieces according to the method of the present invention.

FIG. 20 illustrates profiles of the normal structural stress as the fatigue test data from the foregoing test pieces, where the results are neatly plotted in a smaller band width.

The procedure of estimating the fatigue life of the spot welded structure according to the present invention is illustrated as a flowchart of FIG. 21.

(1) A shell model is prepared as the spot welded structure and subjected to the finite element method elastic analyzing process.

(2) The deflection at desired nodes on the circumference of a circle in which the nugget interest is provided at the center as well as the partial loads exerted on the nugget are calculated.

(3) The nominal structural stress $\sigma_{ns}$ is calculated by the theoretical method described above.

(4) the fatigue life of the spot welded structure is then estimated through referring the $\sigma_{ns}$-Nf database produced with the use of a separately prepared DC test piece.

INDUSTRIAL APPLICABILITY

As set forth above, the fatigue life estimating method for a spot welded structure is characterized in that a disk having a diameter of D and including the nugget of interest at the center is separated from the spot welded structure and stained at the outer edge when loaded at the nugget with partial forces of peel load, bending moment, shear load, and torsional moment for calculating the nominal structural stress. This allows no database of the D diameter to be needed and the troublesome task for determining an optimum of the D diameter to be eliminated. As the result, the fatigue life of the spot welded structure can be estimated easily and readily.

The fatigue life estimating method for a spot welded structure is also characterized in that the two or more plates are at least a flat plate and an L channel while the shell model for the finite element method analyzing process is marked with a square having one side arranged equal to the flange width of the L channel and including the nugget at the center, the square divided radially by two at the nugget, radially by four at the other area than the nugget, and circumferentially by eight. Accordingly, the fatigue life of the spot welded structure can be estimated easily and readily.

The fatigue life estimating method for a spot welded structure is further characterized in that the step of estimating the fatigue life of the spot welded structure includes subjecting the spot welded structure to a tensile shear fatigue test, a peal fatigue test, and a component load fatigue test to produce a map representing the relationship between the nominal structural stress and the number of cycles to fracture and determining the number of cycles to fracture at the nominal structural stress through examining the map. Accordingly, the fatigue life of the spot welded structure can be estimated accurately.

What is claimed is:

1. A fatigue life estimating method for a spot welded structure comprising the steps of:
preparing a spot welded structure consisting of two or more plates joined together;
providing a shell model from the spot welded structure for a finite element method analyzing process;
subjecting the shell model to the finite element method analyzing process to calculate the peel load, the bending moment, the shear force, and the torsional moment as partial forces exerted on a nugget at the center of the spot welded structure as well as the deflection on the circumference of a circle which is D in the diameter and defined to have the nugget at the center;

calculating the nominal structural stress responsive to the peel load, the bending moment, the shear force, and the torsional moment using a disk bending theory and a two-dimensional elastic theory of the elastodynamics with the calculations of the partial loads and the deflection, where components $\sigma_r$, $\sigma_\theta$, and $\tau_{r\theta}$ of the nominal structural stress responsive to the shear force and the torsional moment are calculated using a two-dimensional elastodynamics formula $$\sigma_r = a_0 r^{-2} + 2b_0 + \left(\frac{a_1}{r} + 2b_1 r - 2a_1' r^{-3} + b_1' r^{-1}\right)\cos\theta +$$
$$\left(\frac{c_1}{r} + 2d_1 r - 2c_1' r^{-3} + d_1' r^{-1}\right)\sin\theta +$$
$$\sum_{n=2}^{\infty}\left\{\begin{array}{l}a_n n(1-n)r^{n-2} + b_n(n+2-n^2)r^n - \\ a_n' n(1+n)r^{-n-2} + b_n'(-n+2-n^2)r^{-n}\end{array}\right\}\cos n\theta +$$
$$\sum_{n=2}^{\infty}\left\{\begin{array}{l}c_n n(1-n)r^{n-2} + d_n(n+2-n^2)r^n - \\ c_n' n(1+n)r^{-n-2} + d_n'(-n+2-n^2)r^{-n}\end{array}\right\}\sin n\theta$$

$$\sigma_\theta = -a_0 r^{-2} + 2b_0 + (6b_1 r + 2a_1' r^{-3} + b_1' r^{-1})\cos\theta +$$
$$(6d_1 r + 2c_1' r^{-3} + d_1' r^{-1})\sin\theta +$$
$$\sum_{n=2}^{\infty}\left\{\begin{array}{l}a_n n(n-1)r^{n-2} + b_n(n+2)(n+1)r^n + \\ a_n' n(n+1)r^{-n-2} + b_n'(-n+2)(-n+1)r^{-n}\end{array}\right\}\cos n\theta +$$
$$\sum_{n=2}^{\infty}\left\{\begin{array}{l}c_n n(n-1)r^{n-2} + d_n(n+2)(n+1)r^n + \\ c_n' n(n+1)r^{-n-2} + d_n'(-n+2)(-n+1)r^{-n}\end{array}\right\}\sin n\theta$$

$$\tau_{r\theta} = (2b_1 r - 2a_1' r^{-3} + b_1' r^{-1})\sin\theta - (2d_1 r - 2c_1' r^{-3} + d_1' r^{-1})\cos\theta +$$
$$\sum_{n=2}^{\infty}\left\{\begin{array}{l}a_n n(n-1)r^{n-2} + b_n n(n+1)r^n - \\ a_n' n(n+1)r^{-n-2} - b_n' n(n-1)r^{-n}\end{array}\right\}\sin n\theta -$$
$$\sum_{n=2}^{\infty}\left\{\begin{array}{l}c_n n(n-1)r^{n-2} + d_n n(n+1)r^n - \\ c_n' n(n+1)r^{-n-2} - d_n' n(n-1)r^{-n}\end{array}\right\}\cos n\theta$$

where $a_0$ to $d'_n$ are unknown coefficients determined by the loading condition and the boundary condition, and components $\sigma_r$, $\sigma_\theta$, and $\tau_{r\theta}$ of the nominal structural stress responsive to the bending moment and the peel load are calculated from $$\sigma_r = -D_p \frac{6}{t^2}\left[M_{r0} + \sum_{n=1}^{\infty} M_{rfn}\cos n\theta + \sum_{n=1}^{\infty} M_{rgn}\sin n\theta\right]$$

$$\sigma_\theta = -D_p \frac{6}{t^2}\left[M_{\theta 0} + \sum_{n=1}^{\infty} M_{\theta fn}\cos n\theta + \sum_{n=1}^{\infty} M_{\theta gn}\sin n\theta\right]$$

$$\tau_{r\theta} = (1-\nu)D_p \frac{6}{t^2}\left[\sum_{n=1}^{\infty} M_{r\theta fn}\sin n\theta + \sum_{n=1}^{\infty} M_{r\theta gn}\cos n\theta\right]$$

where $$M_{r0} = \frac{d^2 f_0}{dr^2} + \frac{\nu}{r}\frac{df_0}{dr}$$

$$M_{rfn} = \frac{d^2 f_n}{dr^2} + \frac{\nu}{r}\left(\frac{df_n}{dr} - \frac{f_n}{r}n^2\right) \quad (i \geq 1)$$

$$M_{rgn} = \frac{d^2 g_n}{dr^2} + \frac{\nu}{r}\left(\frac{dg_n}{dr} - \frac{g_n}{r}n^2\right) \quad (i \geq 1)$$

-continued $$M_{\theta 0} = \nu\frac{d^2 f_0}{dr^2} + \frac{1}{r}\frac{df_0}{dr}$$

$$M_{\theta fn} = \nu\frac{d^2 f_n}{dr^2} + \frac{1}{r}\left(\frac{df_n}{dr} - \frac{f_n}{r}n^2\right) \quad (i \geq 1)$$

$$M_{\theta gn} = \nu\frac{d^2 g_n}{dr^2} + \frac{1}{r}\left(\frac{dg_n}{dr} - \frac{g_n}{r}n^2\right) \quad (i \geq 1)$$

$$M_{r\theta fn} = -\frac{n}{r}\left(\frac{df_n}{dr} - \frac{f_n}{r}\right) \quad (i \geq 1)$$

$$M_{rgn} = \frac{n}{r}\left(\frac{dg_n}{dr} - \frac{g_n}{r}\right) \quad (i \geq 1)$$

$$f_0 = A_o + B_0 r^2 + C_0 \ln r + D_0 r^2 \ln r$$

$$f_1 = A_1 r + B_1 r^3 + C_1 r^{-1} + D_1 r \ln r$$

$$f_n = A_n r^n + B_n r^{-n} + C_n r^{n+2} + D_n r^{-n+2}$$

$$g_1 = A_1' r + B_1' r^3 + C_1' r^{-1} + D_1' r \ln r$$

$$g_n = A_n' r^n + B_n' r^{-n} + C_n' r^{n+2} + D_n' r^{-n+2}$$

where r and θ are the polar coordinates, E is the Young's modulus, $\nu$ is the Poisson's ratio, t is the thickness, and $A_0$ to $D'_n$ are unknown coefficients determined by the loading condition and the boundary condition; and estimating the fatigue life of the spot welded structure from the nominal structure stress.

2. A fatigue life estimating method for a spot welded structure according to claim 1, wherein the two or more plates are at least a flat plate and an L channel while the shell model for the finite element method analyzing process is marked with a square having one side arranged equal to the flange width of the L channel and including the nugget at the center, the square divided radially by two at the nugget, radially by four at the other area than the nugget, and circumferentially by eight.

3. A fatigue life estimating method for a spot welded structure according to claim 1 or 2, wherein the step of estimating the fatigue life of the spot welded structure includes subjecting the spot welded structure to a tensile shear fatigue test, a peal fatigue test, and a component load fatigue test to produce a map representing the relationship between the nominal structural stress and the number of cycles to fracture and determining the number of cycles to fracture at the nominal structural stress through examining the map.

4. A fatigue life estimating method for a spot welded structure according to claim 1 wherein said nominal structural stress is a function responsive to not only the shear force (F) and the torsional moment (Mz), but also responsive to the deflections u and v along the directions of γ and θ respectively of polar coordinates on the circumference of assumed spot diameter, and said deflections u and v are calculated from the distortions $\epsilon_r$ and $\epsilon_\theta$ along the directions of γ and θ respectively, based on an equation $$\epsilon_r = \frac{\partial u}{\partial r}$$

$$\epsilon_\theta = \frac{u}{r} + \frac{1}{r}\frac{\partial v}{\partial \theta}.$$

* * * * *